Figure 1:
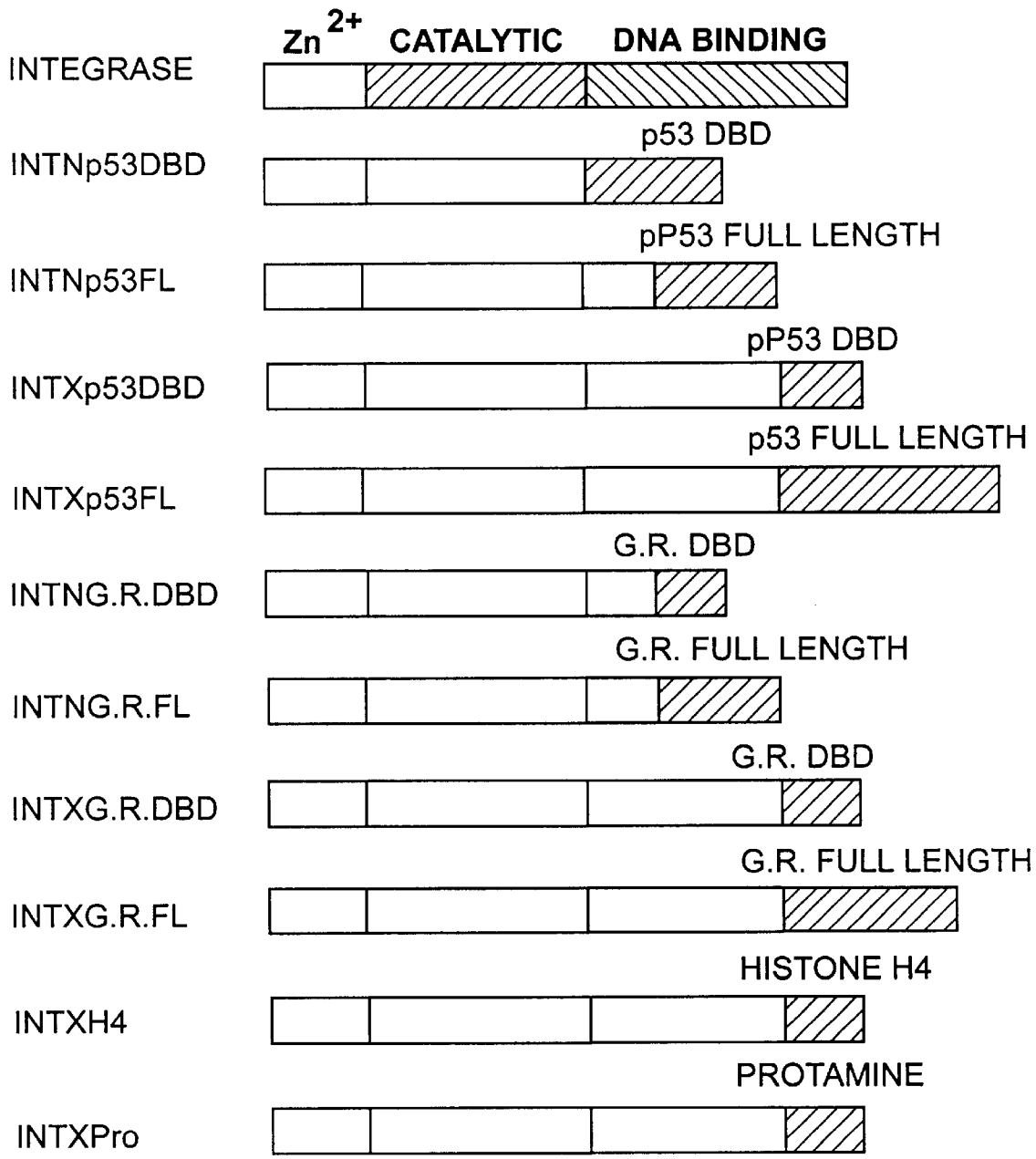

US006139833A

United States Patent [19]
Burgess et al.

[11] Patent Number: 6,139,833
[45] Date of Patent: Oct. 31, 2000

[54] TARGETED GENE DISCOVERY

[75] Inventors: Rob Burgess, Houston; Glenn Friedrich, The Woodlands; Brian Zambrowicz, The Woodlands; Arthur Sands, The Woodlands, all of Tex.

[73] Assignee: Lexicon Genetics Incorporated, The Woodlands, Tex.

[21] Appl. No.: 08/907,598

[22] Filed: Aug. 8, 1997

[51] Int. Cl.[7] .......................... A01N 63/00; A61K 39/00; C12Q 1/68; C12N 1/20

[52] U.S. Cl. .................... 424/93.2; 424/93.6; 424/184.1; 424/199.1; 435/6; 435/235; 435/243; 435/252.3

[58] Field of Search ............... 435/69.7, 235.1, 435/320.1, 69.1, 70.1, 71.1, 6

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,889,818 | 12/1989 | Gelfand et al. | 435/194 |
| 4,965,188 | 10/1990 | Mullis et al. | 435/6 |
| 5,023,171 | 6/1991 | Ho et al. | 435/6 |
| 5,066,584 | 11/1991 | Gyllensten et al. | 435/91 |
| 5,075,216 | 12/1991 | Innis et al. | 435/6 |
| 5,079,352 | 1/1992 | Gelfand et al. | 536/27 |
| 5,091,310 | 2/1992 | Innis | 435/91 |
| 5,104,792 | 4/1992 | Silver et al. | 435/6 |
| 5,464,764 | 11/1995 | Capecchi et al. | 435/172.3 |
| 5,830,707 | 11/1998 | Bushman | 435/69.7 |

FOREIGN PATENT DOCUMENTS

| | | | |
|---|---|---|---|
| 9637626 | 11/1996 | WIPO | C12N 15/90 |

OTHER PUBLICATIONS

M. Barinaga, Knockout Mice: Round Two, Science, vol. 265, pp. 26–28, Jul. 1994.

Mullins et al. Perspectives Series: Molecular Medicine in Genetically Engineered Animals: Transgenesis in the Rat and Larger Mammals. J. Clinical Investigation. vol. 98. No. 11, Supplement, pp. S37–S40, 1996.

Moreadith et al. Gene targeting in embryonic stem cells the new physiology and metabolism. J. Mol. Med. vol. 75, pp. 208–216, 1997.

Bushman et al., 1997, "Tethering Human Immunodeficiency Virus Type 1 Preintegration Complexes to Target DNA Promotes Integration at Nearby Sites", *Journal of Virology*, p. 458–464.

Goulaouic et al., 1996, "Directed Integration of Viral DNA Medicated by Fusion Proteins Consisting of Human Immunodeficiency Virus Type 1 Integrase and *Escherichia coli* LexA Protein", *Journal of Virology*, p. 37–46.

Miller et al., 1995, "Target DNA capture by HIV–1 integration complexes", *Current Biology*, vol. 5, No. 9, pp. 1047–1056.

Akam, 1987, "The molecular basis for metameric pattern in the Drosophila embryo", *Development 101:*1–22.

Akagi et al., 1997, "Cre–mediated somatic site–specific recombination in mice", *Nucleic Acids Res 25:*1766–1773.

Allen et al., 1988, "Transgenes as probes for active chromosomal domains in mouse development", *Nature 333:*852–855.

Barinaga, 1994, "Knockout Mice: Round Two", *Science 265:*26–28.

Barnes and Adcock, 1993, "Anti–inflammatory actions of steroids: molecular mechanisms", *TiPS Reviews 14:*436–441.

Bellen et al., 1989, "P–element–mediated enhancer detection: a versatile method to study development in Drosophila", *Genes & Development 3:*1288–1300.

Bier et al., 1989, "Searching for pattern and mutation in the Drosophila genome with a P–lacZ vector", *Genes & Development 3:*1273–1287.

Bosselman et al., 1987, "Replication–Defective chimeric Helper Proviruses and Factors Affecting Generation of Competent Virus: Expression of Moloney Murine Leukemia Virus Structural Genes via the Metallothionein Promoter", *Molec. Cell. Biol. 7:*1797–1806.

Botsford et al., 1992, "Cyclic AMP in Prokaryotes", *Microbiol Rev 56:*100–122.

Brenner et al., 1989, "Analysis of mammalian cell genetic regulation in situ by using retrovirus–derived "portable exons" carrying the *Escherichia coli* lacZ gene", *Proc Natl Acad Sci. USA 86:*5517–5521.

Burke et al., 1995, "Hox genes and the evolution of vertebrate axial morphology", *Development,* 121:333–346.

Bushman, 1994, "Tethering human immunodeficiency virus 1 integrase to a DNA site directs integration to nearby sequences", *Proc Natl. Acad. Sci. USA 91:*9233–9237.

Chakraborty et al., 1993, "Synthetic retrotransposon vectors for gene therapy", *FASEB Journal 7:*971–977.

Chen et al., 1994, "Transcriptional enhancer factor 1 disruption by a retroviral gene trap leads to heart defects and embryonic lethality in mice", *Genes & Development 8:*2293–2301.

(List continued on next page.)

*Primary Examiner*—George C. Elliott
*Assistant Examiner*—Janet Epps
*Attorney, Agent, or Firm*—Finnegan, Henderson, Farabow, Garrett & Dunner, L.L.P.

[57] ABSTRACT

The present invention describes a comprehensive system for gene discovery using retrovirus that have been engineered to exhibit increased accessibility to genomic DNA, or to mutate and identify the chromosomal target sequences of DNA binding proteins. The strategy employs the combination of retroviral integrase/DNA binding protein fusion constructs and gene-trapping methodologies. This novel technology provides the ability to establish proviral integration at any location within the genome. In addition, it allows for the generation of a collection of eukaryotic cells in which each cell contains a mutation in a target gene or sequence for a known DNA binding protein which also allow for rapid in vivo functional analysis. Sequence information obtained for genes identified using the described methods identify a collection of eukaryotic genes related by, or directly or indirectly regulated by, a given DNA binding protein.

6 Claims, 10 Drawing Sheets

OTHER PUBLICATIONS

Chen et al., 1994, "Large Exon Size Does Not Limit Splicing In Vivo", *Molecular and Cellular Biology 14:*2140–2146.

Coulondre et al., 1977, "Genetic Studies of the lac Repressor", *J Mol Biol 117:*577–606.

Dadoune, 1994, *Bull Assoc Anat,* 78:33–40.

Danos et al., 1988, "Safe and efficient generation of recombinant retroviruses with amphotrophic and ecotropic host ranges", *Proc. Natl. Acad. Sci. USA 85:*6460–6464.

Erlich, H.A., *PCR Technology: Principals and Applications of DNA Amplification* Stockton Press (1989).

Friedrich et al., 1993, "Insertional Mutagenesis by Retroviruses and Promoter Traps in Embryonic Stem Cells", *Methods in Enzymology 225:*681–701.

Friedrich et al., 1991, "Promoter traps in embryonic stem cells: a genetic screen to identify and mutate developmental genes in mice", *Genes & Development 5:*1513–1523.

Frohman et al., 1988, "Rapid production of full–length cDNAs from rare transcripts: Amplification using a single gene–specific oligonucleotide primer", *Proc Natl. Acad. Sci. USA 85:*8998–9002.

Furth et al., 1994, "Temporal control of gene expression in transgenic mice by a tetracycline–responsive promoter", *Proc Natl. Acad. Sci. USA 91:*9302–9306.

Gasca et al., 1995, "Characterization of a Gene Trap Insertion Into a Novel Gene, cordon–bleu, Expressed in Axial Structures of the Gastrulating Mouse Embryo", *Developmental Genetics 17:*141–154.

Goff, 1987, "Insertional Mutagenesis to Isolate Genes", *Methods in Enzymology,* 151:489–502.

Gossler et al., 1989, "Mouse Embryonic Stem Cells and Reporter Constructs to Detect Developmentally Regulated Genes", *Science 244:*463–465.

Goulaouic et al., 1996, "Directed Intergration of Viral DNA Mediated by Fusion Proteins Consisting of Human Immunodeficiency Virus Type 1 Integrase and *Escherichia coli* LexA Protein", *J. Virol. 70:*37–46.

Graham et al., 1991, "Manipulation of Adenovirus Vectors", *Methods Mol. Biol. 7:*109–128.

Han et al., 1997, "Activation of the transcription factor MEF2C by the MAP kinase p38 in inflammation", *Nature 386:*296–299.

Helene et al., 1992, "Control of Gene Expression by Triple Helix–Forming Oligonucleotides", *Annals N.Y. Acad. Sci. 660:*27–36.

Helene, 1991, "The anti–gene strategy: control of gene expression by triplex–forming–oligonucleotides", *Anticancer Drug Des. 6:*569–584.

Hope, 1991, "'Promoter trapping'" in *Caenorhabditis elegans, Development 113:*399–408.

Houghten et al., 1991, "Generation and use of synthetic peptide combinatorial libraries for basic research and drug discovery", *Nature 354:*84–86.

Ingraham et al., 1990, "A Family of Pou–Domain and PIT–1 Tissue–Specific Transcription Factors in Pituitary and Neuroengocrine Development", *Annu Rev Physiol 52:*773–791.

Innis et al., PCR Protocols: *A Guide to Methods and Applications,* Academic Press (1990).

Katz et al., 1996, "Targeting of Retroviral Integrase by Fusion to a Heterologous DNA Binding Domain: In Vitro Activities and Incorporation of a Fusion Protein into Viral Particles", *Virology 217:*178–190.

Kerr et al., 1989, "Transcriptionally Defective Retroviruses Containing lacZ for the In Situ Detection of Endogenous Genes and Developmentally Regulated Chromatin", *Cold Spring Harbor Symposia on Quantitative Biology,* LIV:767–776.

Khan et al., 1990, "Retroviral integrase domains: DNA binding and the recognition of LTR sequences", *Nucl Acids Res. 19:*851–860.

Kirchner et al., 1995, "Requirement of RNA Polymerase III Transcription Factors for in Vitro Position–Specific Integration of a Retroviruslike Element", *Science 267:*1488–1491.

Kozak, 1989, "The Scanning Model for Translation: An Update", *Journal of Cell Biology 108:*229–241.

Kulkosky et al., 1995, "Activities and Substrate Specificity of the Evolutionarily Conserved Central Domain of Retroviral Integrase", *Virology 206:*448–456.

Lam, K.S. et al., 1991, "A new type of synthetic peptide library for identifying ligand–binding activity", *Nature 354:*82–84.

Levine et al., 1991, "The p53 tumour suppressor gene", *Nature 251:*453–456.

Lewin, 1990, "Commitment and Activation at Pol II Promoters: A Tail of Protein—Protein Interactions", *Cell 61:*1161–1164.

Low et al., 1994, "Glucocorticoids Regulate Hippocampal 11β–Hydroxysteroid Dehydrogenase Activity and Gene Expression in vivo in the Rat", *J. Neuroendocrinol. 6:*285–290.

Maher, 1992, "DNA Triple–Helix Formation: An Approach to Artificial Gene Repressors?", *Bioassays 14:*807–815.

Markowitz et al., 1988, "A Safe Packaging Line for Gene Transfer: Separating Viral Genes on Two Different Plasmids", *J. Virol. 62:*1120–1124.

McPherson et al., PCR: A Practical Approach, IRL Press (1991).

Morgan et al., 1996, "Transposon tools for recombinant DNA manipulation: Characterizatoin of transcriptional regulators from yeast, Xenopus, and mouse", *Proc. Natl. Acad. Sci. USA 93:*2801–2806.

No et al., 1996, "Ecdysone–inducible gene expression in mammalian cells and transgenic mice", Proc. Natl. Acad. Sci. USA 93:3346–3351.

O'Banion et al., 1991, "A Serum– and Glucocorticoid–regulated 4–Kilobase mRNA Encodes a Cyclooxygenase–related Protein", *J. Biol. Chem. 266:*23261–23267.

Oudet et al., 1978, *Philos Trans R Soc Lond 283:*241–258.

Picksley et al., 1994, "p53 and Rb: their cellular roles", *Current Opinion in Cell Biology 6:*853–858.

Platt et al., 1994, "Independent Regulation of Adipose Tissue–specificity and Obesity Response of the Adipsin Promoter in Transgenic Mice", *J Biol Chem 269:*28558–28562.

Pryciak et al., 1992, "Nucleosomes, DNA–Binding Proteins, and DNA Sequence Modulate Retroviral Integration Target Site Selection", *Cell 69:*769–780.

Ptashne et al., 1990, "Activators and targets", *Nature 346:*329–331.

Rao et al., 1996, "Lamin Proteolysis Facilitates Nuclear Events During Apoptosis", *J Cell Biol. 135:*1441–1455.

Reddy et al., 1992, "Fluorescence–activated sorting of totipotent embryonic stem cells expressing developmentally regulated lacZ fusion genes", *Proc. Natl. Acad. Sci. USA 89:*6721–6725.

Reddy et al., 1991, "Retrovirus Promoter–Trap Vector To Induce lacZ Gene Fusions in Mammalian Cells", *J Virol 65:*1507–1515.

Rohdewohld, et al., 1987, "Retrovirus Integration and Chromatic Structure: Moloney Murine Leukemia Proviral Integration sites Map Near DNase I–Hypersensitive Sites", *J. Virol. 61:*336–343.

Sabbatini et al., 1997, "Interleukin 1β Converting Enzyme–like Proteases Are Essential for p53–mediated Transcriptionally Dependent Apoptosis", *Cell Growth and Differentiation 8:*643–653.

Sandmeyer et al., 1990, "Integration Specificity of Retrotransposons and Retroviruses", *Annu. Rev. Genet. 24:*491–518.

Sauer et al., 1990, "λ Repressor: A Model System for Understanding Protein–DNA Interactions and Protein Stability", *Adv Protein Chem 40:*1–61.

Shih et al., 1988, "Highly Preferred Targets for Retrovirus Integration", *Cell 53:*531–537.

Skarnes et al., 1992, "A gene trap approach in mouse embryonic stem cells: the lacZ reporter is activated by splicing, reflects endogenous gene expression, and is mutagenic in mice", *Genes & Development 6:*903–918.

Smithies et al., 1985, "Insertion of DNA sequences into the human chromosomal β–globin locus by homologous recombination", *Nature 317:*230–234.

Songyang et al., 1993, "SH2 Domains Recognize Specific Phosphopeptide Sequences", *Cell 72:*767–778.

Thomas et al., 1987, "Site–Directed Mutagenesis by Gene Targeting in Mouse Embryo–Derived Stem Cells", *Cell 51:*503–512.

Thompson et al., 1989, "Germ Line Transmission and Expression of a Corrected HPRT Gene Produced by Gene Targeting in Embryonic Stem Cells", *Cell 5:*313–321.

Valentine et al., 1994, "Glucocorticoids Repress Basal and Stimulated Manganese Superoxide Dismutase Levels in Rat Intestinal Epithelial Cells", *Gastroenterology 107:*1662–1670.

Varmus, 1988, "Retroviruses", *Science 240:*1427–1435.

Vinson et al., 1989, "Scissors–Grip Model for DNA Recognition byb a Family of Leucine Zipper Proteins", *Science 246:*911–916.

von Melchner et al., 1992, "Selective disruption of genes expressed in totipotent embryonal stem cells", *Genes & Dev. 6:*919–927.

von Melchner, 1989, "Identification of Cellular Promoters by Using a Retrovirus Promoter Trap", *J Virol. 63:*3227–3233.

Wright et al., 1989, "Myogenin, a Factor Regulating Myogenesis, Has a Domain Homologous to MyoD", *Cell 56:*607–617.

Yoshida et al., 1995, "A new strategy of gene trapping in ES cells using 3'RACE", *Transgenic Research 4:*277–287.

| | TOTAL SAMPLES | REP. EL. SAMPLES | REPEATS | RATE | OB RATE | p |
|---|---|---|---|---|---|---|
| INTNp53DBD [p53DBD] | 13 | 3 | 2 | 20% | | |
| INTNp53FL [p53 FULL LENGTH] | 6 | 0 | 2 | 33.3% | | |
| INTXp53DBD [p53DBD] | 13 | 2 | 9 | 81.8% | | |
| ALL p53 TARGETS | 32 | 5 | 13 | 51.9% | 7.4% | .005 |

( p VALUES DERIVED FROM FISHER ANALYSIS )

FIG. 8

| | TOTAL SAMPLES | REP. EL. | SAMPLES | REPEATS | RATE | OB | RATE | $p$ |
|---|---|---|---|---|---|---|---|---|
| G.R.DBD | 187 | – | 13 | 174 | 14% | | 5% | <.02 |
| INTNG.R.DBD | | | | | | | | |
| G.R.DBD | 73 | – | 5 | 68 | 12% | | 5% | 0.1 -.02 |
| INTXG.R.DBD | | | | | | | | |

NOTE: $p$ VALUES DERIVED FROM $\chi^2$ ANALYSIS

FIG. 9

A. BLAST RESULTS FOR p53 TRAPPED EXONIC SEQUENCE DISPLAYING HOMOLOGY TO RAT ICE.

```
QUERY:      1    GGGGAAGAAAGGGTTAATTCGACTTACCCTTCCACATTG
                 |||||||||||| ||| | |||| |||||||||||||||
SUBJECT: 3607    GGGGAAGAAAGGGTTATTTGGCTTACACTTCCACATTG

QUERY:     40    TTGTTCATCACCAAGGAATTCAGGACTGGAACTCAATCA
                 ||||||||||||||||| ||| ||| || |||||| ||
SUBJECT: 3646    CTGTTCATCACCAAATGAGTCAGAACAGGAACTCACACA

QUERY:     79    GGTCTGGAAGCATGAGCTGAT
                 || ||||||||| |||||||
SUBJECT: 3685    GGGCAGGAAGCAGGAGCTGAT
```

B. INTRONIC LOCATION OF VIRAL INTEGRATION SITE AND CORRESPONDING OBSERVED p53 BINDING SITE (INDICATED IN BOLD)

```
2761    AAATTATAGAACTACACTGTACATTATTCTGATTGGTTTTTTGTTT
2808    GTTTTTGTTTGCTTGATTTTAAGATACAGTCTCACTATTTAGAC
2855    AGGCTAGCCTCCAGCTTACAAAGATCTGCCTGCCTCTGCTCCCTG
2900    TGTGGTGGGACTAAAGGCATGCGCTACCCCACCCCCAGCTGCTTA
```

FIG. 10

TARGETED GENE DISCOVERY

1.0. FIELD OF THE INVENTION

The present invention relates to the identification and mutagenesis of target genes for DNA binding proteins using mutagenic virus incorporating chimeric integrase proteins.

2.0. BACKGROUND OF THE INVENTION

A key feature of the retroviral replication cycle is that the virus integrates into the host chromosome. Retroviral DNA integration was initially thought to occur in an essentially random manner, for the most part giving no preference to any particular nucleotide sequence as a target for proviral establishment. It has also been suggested that the observed randomness of integration is due to the nonspecific DNA binding affinity of the integrase protein (Sandmeyer et al., 1990; *Annu Rev Genet,* 24:491–518). However, it has recently been reported that retrovirus may exhibit a propensity for integrated into highly preferred target sites (Pryciak and Varmus, 1992, *Cell,* 69:769–80; Rohdewohld, et al., 1987, *Journal of Virology,* 61:336–343; Shih et al., 1988, *Cell,* 53:531–537). This nonrandom integration may result from the restricted access of retroviral integrase protein to genomic DNA, or an interaction with specific target sequences. In general, the observed integration bias has hindered efforts to randomly saturate the mammalian genome with proviral tags (Sandmeyer et al., 1990, *Annu Rev Genet,* 24:491–518).

Experimentally, Bushman et al. has used an artificial system to further bias the integration reaction in vitro using a retroviral integrase that has been fused to the DNA binding domains of the bacteriophage Lambda DNA binding repressor protein using an in vitro integration system. These fusion proteins proved capable of directing retroviral integration into sequences adjacent to Lambda repressor DNA binding sites (Bushman, 1994, *Proc Natl Acad Sci, USA,* 91:9233–9237; Goulaouic and Chow, 1996, *Journal of Virology,* 70, No. 1:37–46). Other groups have expanded on this concept by establishing mutant viral lines containing fusions between the retroviral integrase and the well characterized procaryotic DNA binding protein LexA (Goulaouic and Chow, 1996, *Journal of Virology,* 70, *No.* 1:37–46; Katz et al., 1996, *Virology* 217:178–190). The preliminary in vitro studies using a single procaryotic DNA binding activity provide proof in concept that engineered integrase molecules can mediate nonrandom integration in an artificial biochemical assay. However, the useful application of chimeric integrase would ideally require the following scientific breakthroughs: 1) The production of a chimeric integrase that incorporates a DNA binding domain from a biologically relevant protein with known function in the target cell; 2) The demonstration that the chimeric integrase may be incorporated into an infectious viral particle; 3) The demonstration that the presence of the chimeric integrase does not interfere with reverse transcription; 4) A showing that the chimeric integrase retains the ability to process the inverted repeats at both ends of the retroviral DNA product of reverse transcription; and 5) The demonstration that the chimeric integrase can direct the nonrandom, or biased, integration of the retroviral genome to targeted regions of the cellular genome. Additionally, the above studies require the development of specialized retroviral packaging cell lines, and preferably amphotropic packaging cell lines, that express and incorporate the chimeric integrase molecules into high titer stocks ($>10^5$ per ml) of infectious virus.

The use of modified retroviral vectors to both trap and mutate genes has allowed for the identification of novel genes as well as the analysis of corresponding mutant phenotypes (Chen et al., 1994, *Genes & Development* 8:2293–2301; Gasca et al., 1995, *Developmental Genetics,* 17:141–154; von Melchner, 1989, *J Virol,* 63:3227–3233). Recent advances in vector technology have resulted in the development of efficient gene-trap strategies that have enabled researchers to both discover and disrupt genes (von Melchner et al., 1992, *Genes & Dev* 6:919–927; Yoshida et al., 1995, *Transgenic Research* 4:277–287). Although such approaches have yielded a sizable amount of raw genetic information, the general absence of practical genetic systems in most higher eukaryotes has largely prevented researchers from organizing the raw data into regulatory hierarchies. Consequently, only a minor fraction of the mammalian gene products identified from DNA sequence data have been functionally defined in the context of the biochemical pathways or regulatory cascades in which they are involved.

By developing the technological breakthroughs necessary for the biologically relevant exploitation of chimeric integrase molecules, and further combining targeted integration with high efficiency gene trap technology, the present invention defines a novel and improved method of gene discovery. A method that allows for the rapid identification, cloning, sequencing, and disruption of genes in proximity to, encoding, or regulated by, DNA binding protein target sequences.

3.0. SUMMARY OF THE INVENTION

The present invention describes the first demonstration of targeted gene discovery in animal cells. In addition to tools and methods for guiding integration to specific DNA targets in chromatinized DNA, the present invention also describes methods for enhancing the general accessibility of the cellular genome to retroviral integration and mutation.

Additional objects of the present invention include methods for the rapid identification and mutagenesis, via gene trapping, of genes encoding, regulated by, or adjacent to, target sequences for DNA binding proteins.

An additional embodiment of the present invention is a process for identifying and defining genetic pathways in a cell comprising using a virus incorporating a chimeric integrase to trap a gene regulated by the product from which the specific DNA binding activity of the chimeric integrase was derived; determining whether the trapped gene encodes a specific DNA binding activity; engineering a second chimeric integrase by fusing the specific DNA binding domain from the trapped gene to a suitable region of the integrase gene; incorporating the second chimeric integrase into a second virus (which may use the same vector as that used in the first round of gene trapping); and using the second virus to trap the gene or genes regulated by the product of the initially trapped gene. By repeating/extending the above process, one may serially trap an entire regulatory cascade, and thus define a given genetic or regulatory pathway.

The chimeric integrase contemplated by the present invention incorporates at least two domains. The first domain encodes an activity that mediates DNA integration into the host chromosome. The second domain of the chimeric integrase encodes a non-retroviral DNA binding activity that homes to naturally occurring target DNA sequences encoded by mammalian cells. The combining of the two domains may be mediated by the generation of DNA constructs encoding the fusion protein, by protein/protein interaction via disulfide bonds or other covalent modifications, by enzymatic crosslinkage, through interaction with an intermediate docking protein or phospholipid between the two domains, through hydrophobic clustering, or any other feasible method which brings the domains together to catalyze both site-specific DNA binding and integration. Optionally, the chimeric integrase can incorporate a third domain, in addition to the integration and DNA binding domains, that encodes a region that binds another protein. Moreover, the protein binding domain can also be incorporated into the chimeric integrase in lieu of the DNA binding domain.

A specific embodiment of the presently described chimeric integrase molecules is a protein fusion between a murine retroviral integrase and the transcription factor p53. Combined with an appropriate retroviral vector, the chimeric integrase fusion protein is packaged into a recombinant retrovirus that is specifically tailored for the identification and mutagenesis of genes involved in tumor suppression (e.g., genes encoding, regulated by, or adjacent to a p53 DNA binding site). This fusion protein contains the domain of the integrase protein that mediates retroviral integration, lacks the carboxy-terminal integrase DNA binding domain, and is fused to the DNA binding domain of p53.

Another integrase-p53 fusion protein contemplated by the present invention is also designed to encode a fusion protein between murine retroviral integrase and the transcription factor p53. This fusion protein contains the domain of integrase required for integration, lacks the integrase DNA binding domain, and is fused to the full-length coding sequence of p53 to further maintain protein/protein involved in p53 function.

A third chimeric integrase contemplated by the present invention is another fusion protein between retroviral integrase and the DNA binding domain of p53. However, this chimeric integrase retains a significant portion of the C-terminal DNA binding domain of the INT protein. While the number of random integration events increases due to the inclusion of the INT DNA binding domain, certain facets of the integration reaction (e.g., end processing and joining capacities) are also enhanced. The enhanced integration efficiency afforded by such molecules results in overall higher viral titers compared to those for obtained using INT fusion proteins that delete the INT DNA binding domain.

A fourth chimeric integrase contemplated by the present invention also encodes a fusion protein between INT and p53 with the fusion junction occurring at the same site as the preceding vector. However, this construct contains a substantially full length coding sequences for p53 to enhance the possibility of p53 mediated protein/protein interactions.

Other chimeric integrases contemplated by the present invention use design strategies similar to those exemplified in the INT-p53 fusions. Instead, the p53 component of the chimeric integrase is replaced by the steroid responsive glucocorticoid receptor. These chimeric integrases are designed to facilitate the identification and mutagenesis (e.g., tagging) of genes involved in steroid response. The fusion junctions in these molecules are similar to that for the INT/p53 constructs.

In view of the above described chimeric integrase activities, an additional object of the present invention is an infectious recombinant virus that is capable of infecting higher eukaryotic cells and incorporates a chimeric integrase activity that has been engineered to target and guide viral integration to specific regions of the genome of living cells (i.e., in vivo). Alternatively, the chimeric integrase may be used in conjunction with nonviral (i.e., where the recombinant vector is not assembled into an infectious virus) means of targeted gene discovery.

An additional chimeric integrase contemplated by the present invention consists of a fusion between INT and histone H4. Fusion occurs at the terminal end of INT, includes full length H4 coding sequences and is constructed to aid in the recruitment of INT to nucleosomal complexes, allowing access to compacted regions of DNA, for integration.

Similarly, another chimeric integrase contemplated by the present invention encodes a fusion between full length INT and protamine-1, a protein known to displace histones at the nucleosomal complex due to its basic characteristics. The fusion includes all protamine coding sequences and occurs at the same fusion junction as that used for histone H4 chimeric integrase. This molecule is also designed to enhance chromatin access.

Another object of the invention is to provide recombinant virus that are capable of infecting higher eukaryotic cells and incorporate chimeric integrase activities that have been engineered to have enhanced DNA binding characteristics that functionally enhance genomic access.

Yet another object of the present invention are mutant viruses capable of infecting murine embryonic stem cells. Preferably, these viruses incorporate chimeric integrase proteins that are capable of guiding integration to, and subsequently mutation and identification, i.e., "gene trapping", specific DNA binding protein target sequences.

A further object of the invention is to provide the vectors from which the mutant virus are derived. Accordingly, the above chimeric integrase are combined with an additional embodiment of the present invention that includes vectors containing LTR sequences ("LTR vectors") sufficient to allow the INT protein to mediate the appropriate integration reaction.

An additional embodiment of the present invention are viral packaging cell lines that express the presently described chimeric integrase molecules in conjunction with, inter alia, an amphotropic envelope protein or an ecotropic envelope protein. After transfection with the a suitable LTR vector, these cells serve as a source of engineered virus for infection of embryonic stem cells, or any of a wide variety of vertebrate animal cells.

Yet another embodiment of the present invention includes the generation of a collection, or library, of mutant animal cells containing integrated retroviral sequences. The integration events will preferably be located in proximity to DNA binding protein target sequences and genes adjacent to these sequences. The collection will serve as a source for obtaining specifically mutated cells, cell lines derived from individually mutated cells, cells for use in the production of transgenic animals, and cells for the production of genomic DNA and mRNA to clone the putative DNA binding protein targets.

4.0. DESCRIPTION OF THE FIGURES

FIG. 1. Shows a diagram of representative fusion proteins generated between the retroviral integrase and the current studied DNA binding proteins.

Figure 2:
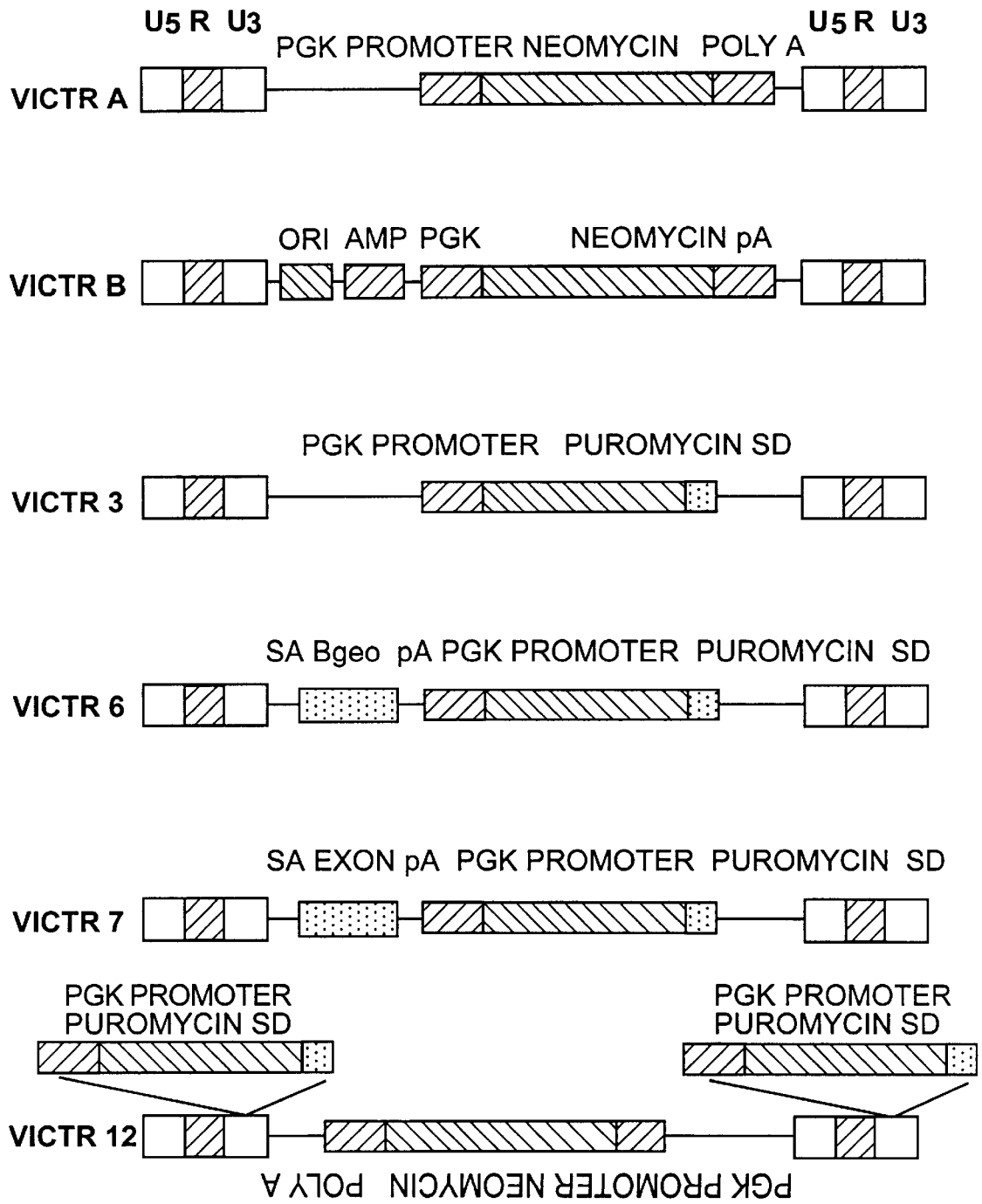

FIG. 2. Shows a diagrammatic representation of the proviral forms of some of the VICTR integration constructs used in the present invention (the neo marker cassette of VICTR 12 is presented upside down because the cassette is in the opposite orientation of the puro marker).

Figure 3:
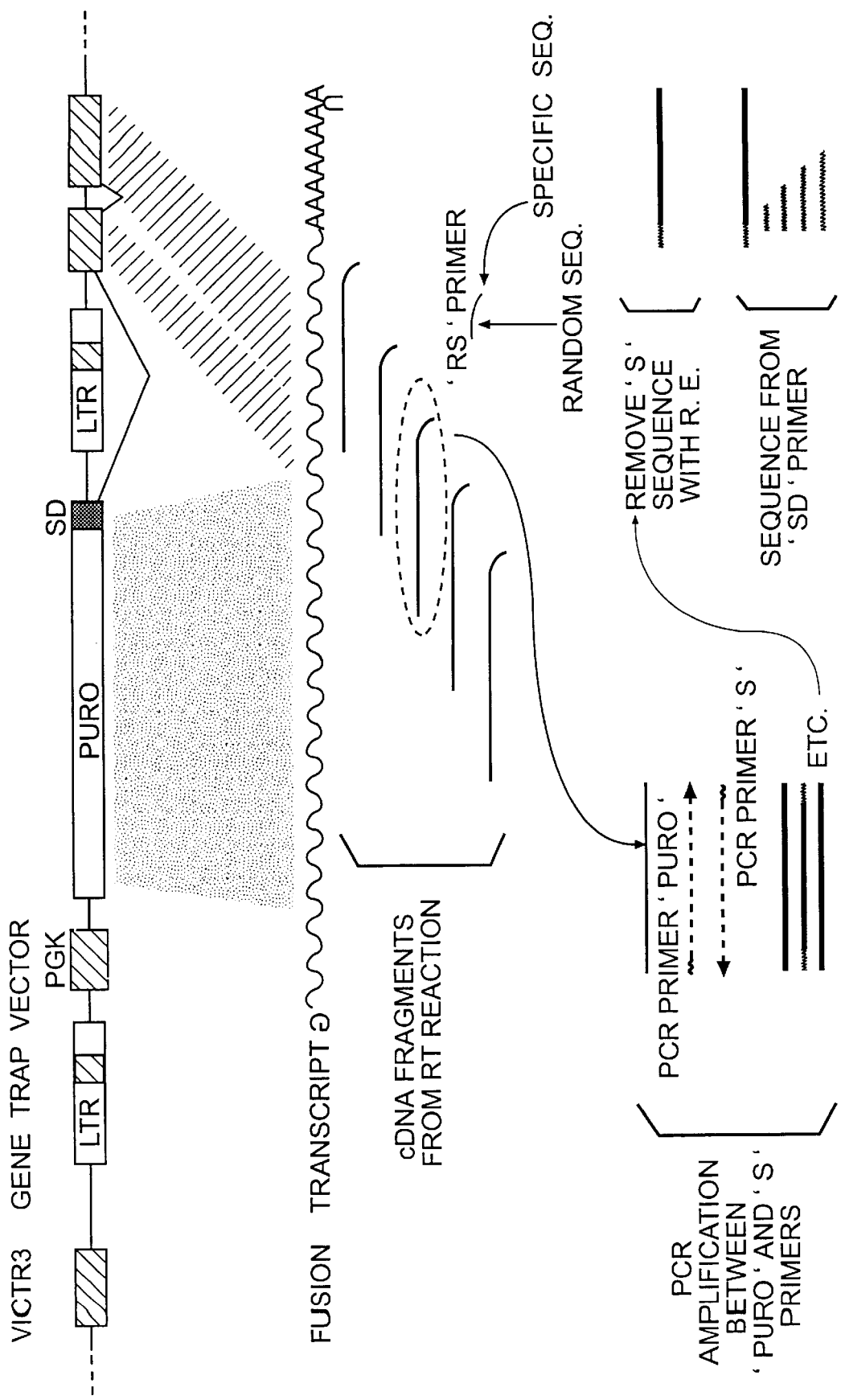

FIG. 3. Outlines a PCR based strategy for the recovery of "trapped" exonic sequences located 3' of the integration site for VICTR 3.

Figure 4:
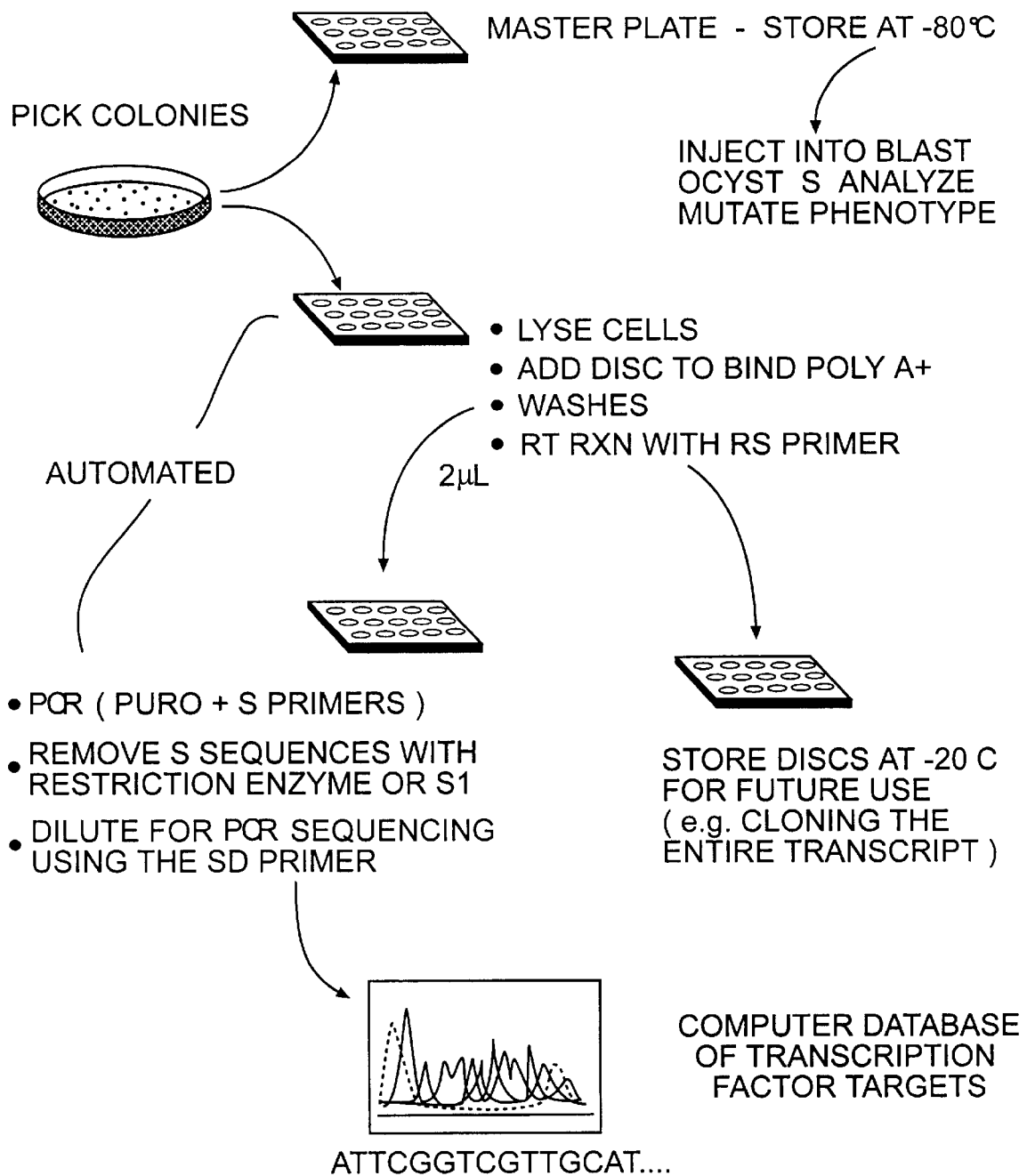

FIG. 4. Is a diagrammatic representation of the overall strategy for establishing a database and constructing a collection of cells with mutations in DNA binding protein targets.

Figure 5:
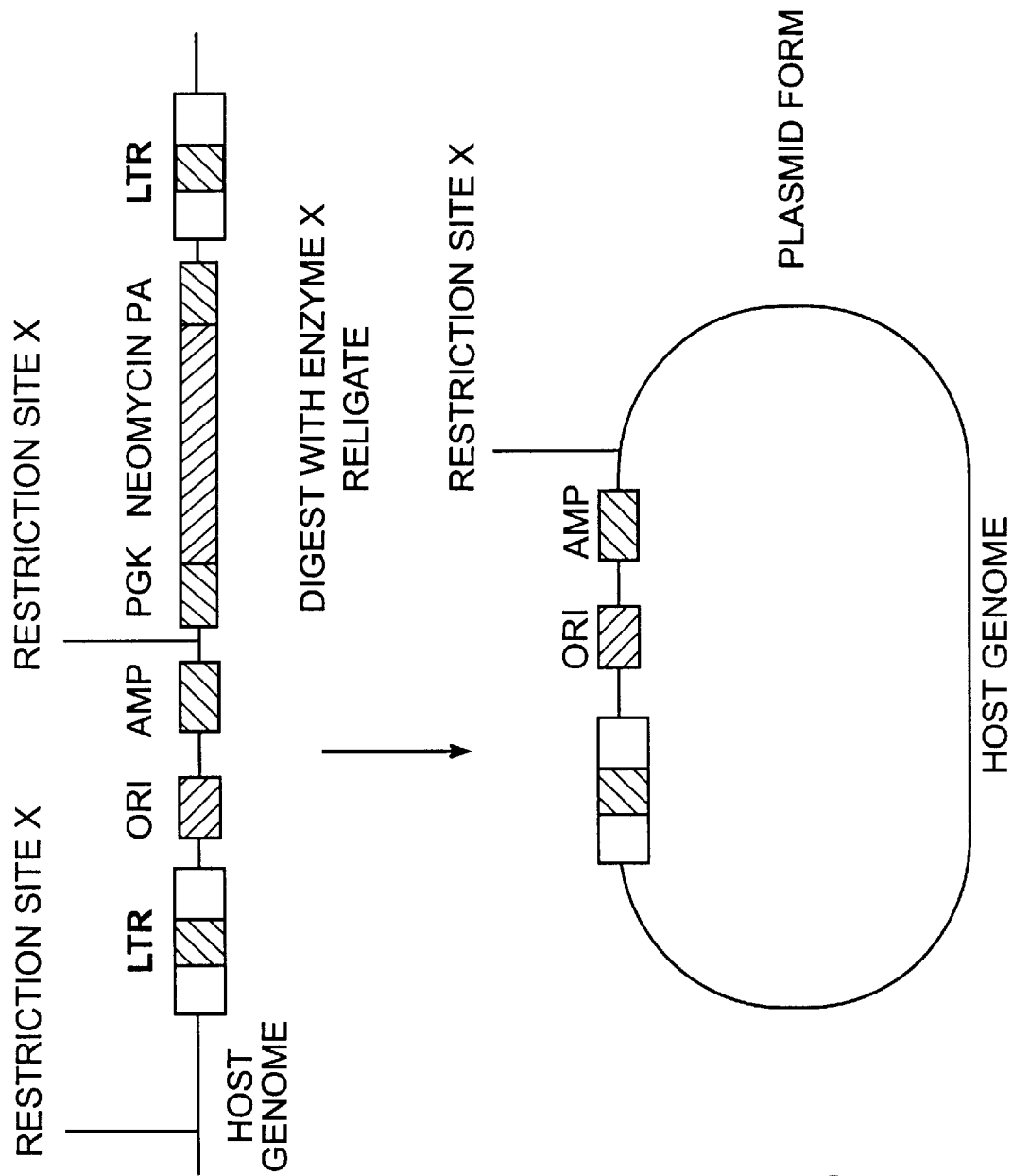

FIG. 5. Is a diagrammatic representation of the strategy for converting the integrated form of VICTR B into plasmid form. VICTR B is illustrated in proviral form. This plasmid product contains sequences flanking the genomic integration site.

Figure 6:
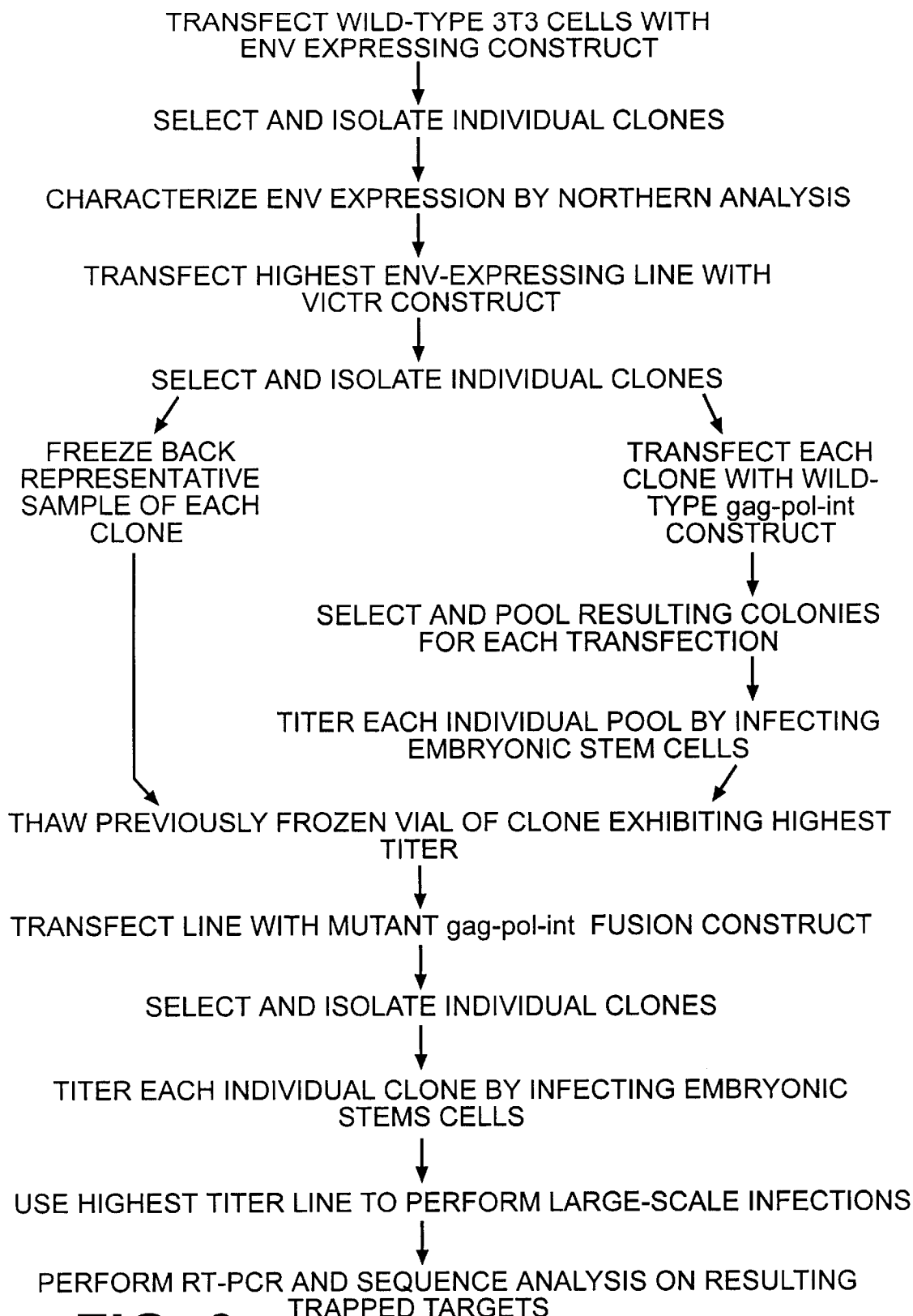

FIG. 6. Is an outline of the strategy utilized to acquire exceptionally high titer viral stocks containing mutant integrase and gene-trapping constructs.

Figure 7:
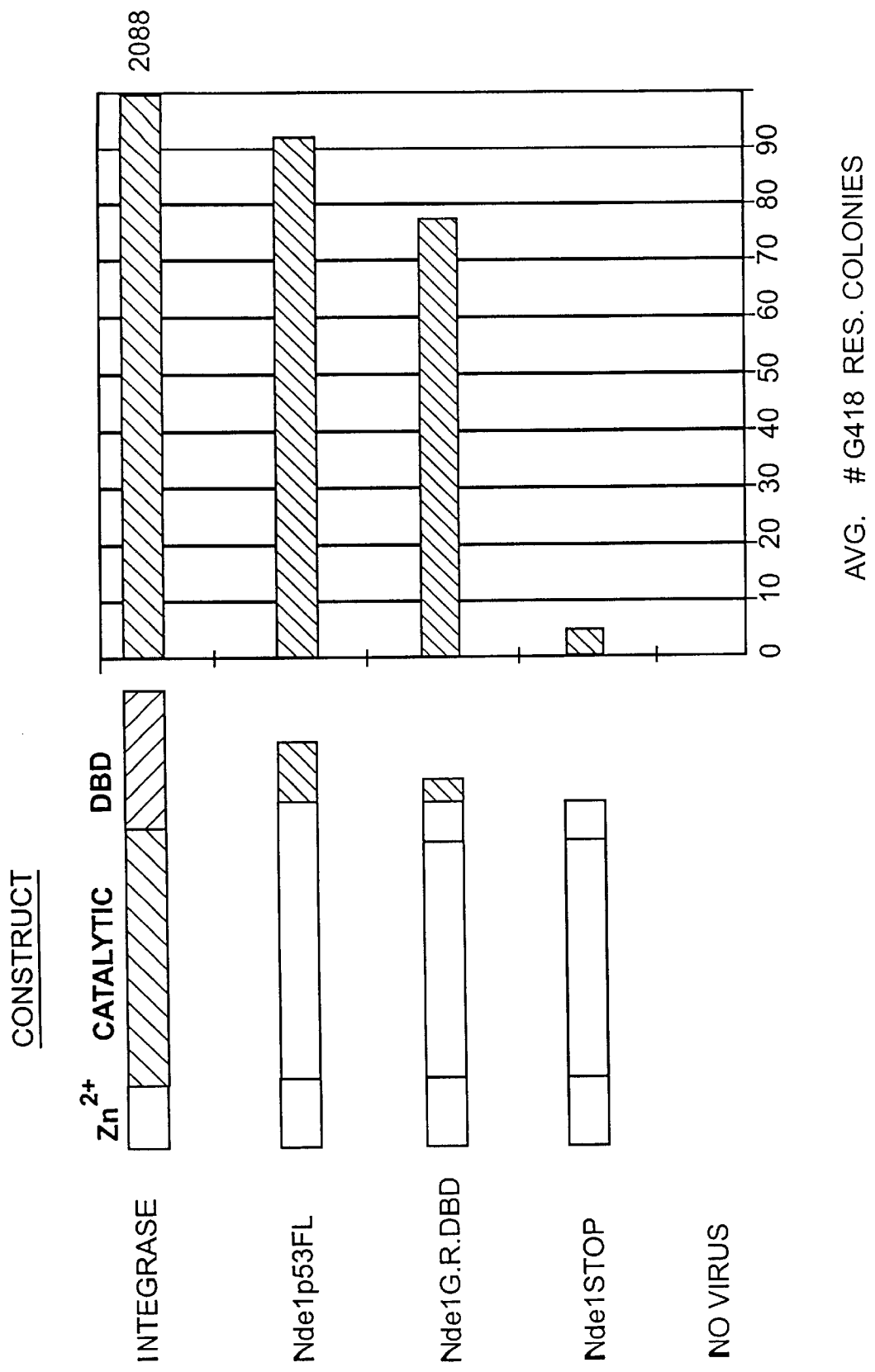

FIG. 7. Is a graphic illustration of the partial rescue of truncated integrase integration capability by the addition of transcription factor sequences to the truncated site. (see text for details).

FIG. 8. Depicts the repeat rates observed for wild-type and mutant INT/p53 viruses used to generate the collection of mutated trapped target genes. Each INT/p53 fusion construct is diagrammatically illustrated to the left (see text for details).

FIG. 9. Depicts the repeat rates observed for wild-type and mutant INT/G.R. viruses used to generate the collection of mutated trapped target genes. Each INT/G.R. fusion construct is diagrammatically illustrated to the left (see text for details).

FIGS. 10A–10B. A. Shows an example of an INT/p53 target gene trapped using mutant viruses (SEQ ID NO:1–6). B. Displays the intronic region and p53 binding site of the target locus in which integration occurred (SEQ ID NO:7–10; see text for details).

5.0. DETAILED DESCRIPTION OF THE INVENTION

The current invention illustrates a method for the targeted identification and disruption of DNA binding protein target genes and sequences. It involves the use of virus harboring a chimeric retroviral integrase/DNA binding protein in combination with an LTR vector (preferably a gene trapping vector). After infection, the DNA binding activity engineered into the chimeric integrase guides the integration of the LTR vectors to defined regions of genomic DNA, i.e., regions flanking the binding protein recognition sequence. By combining guided integration with novel gene trapping methodologies, the present invention describes a unique tool for the rapid and efficient identification and mutation of eukaryotic genes.

Typically, the chimeric integrase molecules of the present invention are engineered to target integration to naturally occurring DNA sequences present in animal cell chromosomes. Although the target cells may be transformed, polyploid, or aneuploid, a preferred embodiment of the present invention includes using a chimeric integrase to target integration into cells comprising a normal genetic complement (a number of chromosomes typical of a given somatic, germ line, or stem cell for a given species). Moreover, a particularly preferred embodiment of the present invention involves the use of a chimeric integrase to target integration into target DNA sequences that naturally occur in the chromosomes of cells that are suitable for implantation in vivo.

Alternatively, the specific DNA binding activity of the chimeric integrase may be replaced, or supplemented, with DNA binding domains from highly basic chromatin binding proteins. Presumably, the inclusion of these domains will enable access to regions of dense chromatin that are typically under represented in normal libraries generated using retrovirus incorporating "normal" integrase activities. Thus, chimeric integrase with such enhanced DNA binding activity effectively render a larger portion, if not all, of the genome accessible to proviral gene disruption or gene trapping.

Vectors suitable for use in the present invention typically include sequences necessary for integrase-mediated processing and integration. In particular, the inverted repeat regions of the viral LTRs are important elements of the specifically described recombinant retroviral vectors. For the purposes of the present invention, the term "recombinant" refers to engineered biopolymers (e.g., polynucleotides or polypeptides) of which any portion of the sequences or sequence organizations contained therein are not naturally occurring.

Where the vector encoded transcripts are to be packaged into infectious retroviral particles incorporating chimeric integrase, the LTR vector must encode a Psi packaging sequence. For the purposes of the present disclosure, the term "infectious virus" shall mean that an assembled virus, or the genetic complement packaged within an assembled virus, is capable of infecting a target cell where the virally encoded material is directly (in the case of a DNA virus), or indirectly (as in the case of a retrovirus) expressed by the infected cell. Although infectious virus may be replication competent, for the purposes of the present invention a virus need not be replication competent to be considered "infectious".

Specific examples of LTR vectors suitable for use in the present invention include, but are not limited to, gene trapping constructs comprising selectable marker genes that remain inactive unless particular properties are provided by endogenous cellular sequences that flank the vector after integration. Such factors necessary for marker expression include, but are not limited to, polyadenylation signals, active promoters, as well as splice donor and splice acceptor sequences.

Retrovirus package an RNA genome that serves as a template for the production of a DNA genome (via reverse transcription) that goes on to form the integrated proviral genome during retroviral infection. Accordingly, for the purposes of the present invention it is to be understood that a retroviral RNA genome "encodes" a relevant polynucleotide sequence element (e.g., promoter, intron, gene, splicing signals, polyadenylation site, etc.) when the corresponding proviral DNA sequence the encodes the relevant sequence elements. Similarly, a retroviral genome "encodes" the relevant order, position, or organization of sequence elements when the corresponding integrated provirus manifests the relevant order, position, or organization of sequence elements.

One of the LTR vectors specifically contemplated by the present invention is a vector designed to allow for selection and identification of cells into which the vector has integrated. This LTR vector contains a constitutively active promoter located 5' to a selectable marker which has a polyadenylation site located at its 3' end.

An additional LTR vector contemplated by the present invention is a vector designed to trap exonic sequences through the insertion of foreign exons upstream of endogenous exons in animal cell transcripts. This LTR vector also allows for the selection and identification of the cells in which gene trapping, or integration, has occurred. This LTR vector consists of a constitutively active promoter element positioned 5' to a selectable marker that contains a splice donor (SD) sequence positioned at the 3' of the marker gene. Expression of the selectable marker requires that the splice donor site be used to splice the marker transcript to an endogenous transcript containing a polyadenylation site.

Another LTR vector contemplated by the present invention is a vector encompassing two different selectable markers to allow for the selection of both successful integration of said vector and putative exon trapping. A constitutively active promoter element is located 5' of one of these selectable markers and a polyadenylation site is located at its 3' end. The second selectable marker has a constitutively active promoter located 5' in a similar manner to that of the first selectable marker. In addition, this vector possesses a splice donor sequence located at its 3' end and lacks a polyadenylation signal.

A fourth LTR vector contemplated by the present invention is a vector designed to facilitate the cloning of sequences flanking the integration site. This vector contains a bacterial ColE1 origin of replication and also includes a selectable marker that allows one to select for growth of rescued clones in bacterial cells. In addition, the vector contains a selectable marker containing a constitutively active promoter at its 5' end and a polyadenylation site at its 3' end.

A fifth LTR vector contemplated by the present invention is a vector designed to trap exonic sequences. This vector contains a selectable marker that is present in the LTR regions. These markers lack both an initiator methionine and a polyadenylation signal. Successful integration into exons and the endogenous transcription of resulting in-frame fusions of the selectable marker within genomic open reading frames signals the successful trapping and mutagenesis of target gene exonic sequences.

A sixth LTR vector contemplated by the present invention is a vector designed to trap exonic sequences located 3' of the integration site. It consists of a constitutively active promoter located 5' of a selectable marker sequence positioned within the LTR; however, the vector lacks a splice donor sequence and must therefore be integrated within exonic sequences in order to be properly expressed.

A seventh LTR vector contemplated by the present invention is a vector designed to trap exonic sequences located either 5' or 3' of the integration site. Said vector contains a constitutively active promoter located 5' of a selectable marker containing a consensus splice donor site at its 3' end and lacking a polyadenylation signal (for trapping 3' exons), as well as a promoterless selectable marker containing a polyadenylation site and possessing a consensus splice acceptor sequence located at its 5' end (for trapping 5' exons).

An additional embodiment of the present invention is a collection of eukaryotic cells, each containing a mutation in a gene regulated by the DNA binding protein used to construct the chimeric integrase incorporated into the mutagenic virus used to infect the collection of cells, as well as procedures for establishing and utilizing the same. Each cell in the collection of cells, or library, contains at least one mutation (and preferably a single mutation) caused by the insertion of the vector sequence. Individual cells from the library may be clonally expanded, and cellular sequences flanking the inserted vector, or the sequences of cellular exons spliced to the vector encoded transcripts, can be obtained for the mutated genes. Using this methodology, a DNA sequence library of related sequences may be generated and catalogued. These libraries are result from the guided mutagenesis resulting from combining the integration activity of the INT protein, or related proteins, with specific DNA binding activities/domains from any of a variety of transcription factors. Accordingly, the presently described invention also provides for the mutagenesis of essentially every gene thought to be a target for a particular DNA binding protein. For the purposes of the present invention, the term "essentially every gene" shall refer to the statistical situation where there is generally at least about a 50 percent probability that a comprehensive set of targets for a given DNA binding protein contain at least one inserted vector sequence in each target gene, typically at least about a 70 percent probability, preferably at least about an 85 percent probability, and more specifically at least about a 95 percent probability as determined by a standard Poisson distribution.

Additional embodiments of the present invention are libraries that take advantage of the increased accessibility to regions of chromatin afforded by the disclosed chimeric integrase molecules. These libraries are enriched for sequences normally unavailable for proviral establishment due to specific structure and sequence characteristics, or sequences that are under represented in conventionally generated libraries because of the nonrandom patterns of mutagenesis associated with the observed bias in integration efficiency. The presently described strategy allows for retroviral integration and provirus formation to occur at essentially any location within the genome. For the purposes of the present invention, the term "essentially any location" refers to any nucleosomal or nonnucleosomal region of the genome.

In addition, for the purposes of the present invention, the term "nonrandom integration" refers to the propensity for integration to occur at preferred target sequences for DNA binding proteins. The nonrandomness of said integration is determined mathematically by comparing the mean of the population to the standard deviation of the same population of mutants by Southern analysis. The nonrandomness of said integration is also determined statistically by obtaining the sequence of mutated genes and comparing samples within a population to delineate repeat hits. Finally, the nonrandomness of said integration is determined by cloning and sequencing host regions of DNA located proximal to the integrated vectors (i.e., generally within about 1 to about 3 kb of either end of the integrated vector/polynucleotide, or host exons spliced to vector encoded transcripts) to determine the presence or absence of the aforementioned protein binding site. For the purposes of the present disclosure, the term "guided integration" shall refer to those situations where the observed distribution of mutants obtained with a chimeric integrase, differs from the distribution of mutants obtained using naturally occurring INT activities by at least about one standard deviation, and preferably by at least two standard deviations.

Also for the purposes of the present invention, the term "gene" shall refer to any and all discrete coding regions of the a the cellular genome, as well as associated noncoding and regulatory regions. Additionally, the term "operatively positioned" shall refer to that fact that processing elements, control elements, or genes are present in the proper orientation and spacing necessary to provide the desired or indicated functions of the processing elements, control elements, or genes.

For the purposes of the present invention, a gene is "expressed" when a control element in the cell mediates the production of functional or detectable levels of mRNA encoded by the gene, or a selectable marker inserted therein. A gene is not expressed where the control element in the cell is absent, has been inactivated, or does not mediate the production of functional or detectable levels of mRNA encoded by the gene, or a selectable marker inserted therein.

5.1 Constructs encoding fusion proteins used to generate a library of cells.

The process of proviral establishment via the proper integration of retroviral DNA into the host genome has been well documented (Varmus, 1988, *Science,* 240:1427–1435). In addition, the functional domains of retroviral integrase (INT) have previously been identified (Khan et al., 1990, *Nucl Acids Res,* 19:851–60). The retroviral integrase protein consists of an amino terminal DNA binding domain characterized by a "zinc finger" like motif thought to be involved in binding of viral LTRs prior to and during genomic integration. A centrally located catalytic domain contains three acidic residues that are highly conserved among the retroviral and retrotransposon families. This region of INT has been shown to possess both exonuclease and joining activities. A nonspecific DNA binding activity has been associated with the carboxy-terminal portion of INT, and it is thought that this domain is involved in nonspecific interactions with the host cellular sequences. The nonspecific nature of this interaction has been determined from the essentially random pattern of proviral integration and establishment throughout the regions of the host genome that are naturally accessible for proviral integration (Kylkosky et al., 1995, *Virology,* 206: 448–456).

Recently, several groups have demonstrated that the lack of specificity in DNA binding by retroviral integrase may be biased to occur at engineered sites for DNA binding proteins in vitro (Bushman, 1994; Goulaouic and Chow, 1996; Bushman, 1995, see also WO 97/2003, published Jun. 5, 1997, which claims priority to U.S. Provisional Application Ser. No. 60/008,263 both of which are herein incorporated by reference). The site-directed integration observed in these in vitro studies was catalyzed by fusion proteins that combined a retroviral INT protein with a prokaryotic DNA binding protein. The results of the in vitro biochemical assays indicated that the chimeric INT proteins could direct integration into naked (e.g., nonchromatinized) target DNA sequences comprising engineered target sequences. The bacterial or phage DNA binding protein component of chimeric integrase proved capable of biasing in vitro integration reactions to regions within the 30–50 nucleotides flanking the engineered DNA target sequence.

Fusion constructs generated between retroviral integrase and exogenous DNA binding proteins which direct site-specific integration have previously been designed to place the junction between INT and the DNA binding protein in question at both the N- and C-terminal regions of INT. The specific embodiments of present invention described herein exclusively employ fusions to the C-terminal portion of the INT protein. Additional embodiments of the presently described INT chimeras include versions where the nonspecific DNA binding domain of INT has been eliminated. By deleting the naturally occurring nonspecific DNA binding domain, the amount of random integration of viral DNA into the host genome is reduced. This represents a significant improvement and allows for a more efficient and high throughput analysis of target sites. In addition, the chimeric integrase activities disclosed in the present invention are designed such that they can be incorporated into larger fusions with retroviral reverse transcriptase and ultimately be packaged into viral particles. This offers the advantage of allowing targeted or guided integration into living cells (i.e., in vivo).

The described C-terminal fusion proteins of the present invention are positioned at varying sites along the INT carboxy terminus and are depicted in FIG. 1. One such fusion encompasses a chimeric protein between INT and the DNA binding domain (DBD) of the tumor suppressing transcription factor p53. This construct is designed to direct integration proximal to genes transcriptionally regulated by p53. The junction occurs at an NdeI site located in the coding region corresponding to a site 44 amino acids carboxyl to the conserved glutamic acid residue present in the INT catalytic domain, and the resulting chimeric integrase contains amino acids 73–290 of the p53 DNA binding domain. The location of the fusion junction removes the proline rich hinge region of INT, and results in a chimeric INT-p53 protein having a rigid structure. The p53 amino-terminal activation and carboxy-terminal oligomerization domains have been deleted from this chimeric protein to eliminate possible nonspecific interaction with other proteins bound to the DNA duplex. Thus, integration mediated by this chimera should preferentially occur proximal to p53 DNA binding sites as directed by the terminal end of the chimeric protein.

Another construct encoding an INT/p53 chimeric protein has been generated at the NdeI site that retains the full length coding region of p53. By including the activation and oligomerization domains of p53 in addition to the DNA binding region, protein/protein interactions involved in p53 mediated transcriptional activity remain possible. These interactions, in addition to p53 mediated sequence-specific DNA binding, help to further recruit INT to p53 binding sites and further facilitate integration at or near the targeted sequence.

Another fusion construct generated between INT and the p53 DNA binding domain involves a junction between the relevant regions of the two proteins at the C-terminal XmaI restriction site present in INT coding region. This construct contains almost all of the integrase coding region, including the nonspecific DNA binding domain, and maintains INT in an essentially native state. While random integration background is increased using this chimeric protein, the protein's ability to catalyze efficient integration is retained and viral titers similar to those observed using "wild-type" virus are observed.

Additionally, similar fusions between full-length INT and full length p53 have been generated at the XmaI site of INT. These constructs include the majority of the INT as well as p53 coding regions which may facilitate both efficient and end-joining by integrase as well as targeted integration mediated by p53.

In order to define genes involved in steroid response, fusion constructs were generated between INT and the glucocorticoid receptor, a well studied transcription factor involved in the control of inflammation through the transcriptional regulation of steroid response elements (SREs) located within the control regions of certain loci (Barnes and Adcock, 1993, *TIPS* 14:436–441). These constructs are similar to those designed for p53. Both full length as well as the DNA binding domain alone of the glucocorticoid receptor were fused to the Nde1 site of INT, thus eliminating the majority of the DNA binding domain of INT to enhance for integration targeted by the receptor. In a likewise fashion, the DNA binding domain alone and full length glucocorticoid receptor were fused to the terminal XmaI site of INT. Again, these constructs allow for efficient integration by retaining most of the INT coding region (FIG. 1).

An additional chimeric INT constructed for the present invention encodes a fusion between retroviral INT and the nucleosomal protein histone H4 full length coding sequence, specifically at the c-terminal XmaI site of the INT coding region. In its native state, H4 oligomerizes into an octamer complex with other histones. Tight interaction of this oligomer with genomic DNA, due to the protein's highly basic content, results in compaction of the chromatin into nucleosomes (Oudet et al., 1978, *Philos Trans R Soc Lond* 283:241–258). Infectious virus incorporating this chimeric INT are able to integrate into regions of dense nucleosomal chromatin that are largely inaccessible to retroviral integration mediated by native INT.

Similarly, a chimeric INT has been generated which encodes a fusion between retroviral INT and protamine-1, a highly basic protein previously shown to displace histones from the nucleosome (Dadoune, 1994, *Bull Assoc Anat*, 78:33–40). Like the H4 fusion, the XmaI site was used for the fusion junction, and the protein retains most of the INT coding region as well as a full length protamine-1. This chimeric INT also allows integration at essentially any location within the genome.

In addition to the fusion constructs generated between INT and the specifically exemplified transcription factors, additional constructs containing stop codons at the INT/transcription factor fusion junctions have been constructed as controls to assess the background levels of integration obtained in the absence of the transcription factor DNA binding domains.

While the present invention describes both the increased accessibility to the genome as well as the identification of transcription factor targets sequences using the described INT/nucleosomal or INT/transcription factor fusion proteins, the present invention is in no way limited to the specifically exemplified nucleosomal proteins or trans-acting factors. Any additional prokaryotic or eukaryotic proteins that directly bind to DNA or are indirectly recruited to DNA through protein/protein interactions may be used to practice the subject invention. These include other proteins which play roles in the organization of chromatin structure or factors involved in the regulation of embryonic development, cellular fate, cellular commitment, cellular migration, apoptosis, DNA repair and/or replication, cell-cycle and other eukaryotic or prokaryotic entities. Such factors may include, but are in no way limited to the eukaryotic RNA polymerases I, II and III or any protein involved in basal transcription such as TFIID (TATA binding protein) (Lewin, 1990, *Cell*, 61:1191–1164); the basic helix-loop-helix families of transcription factors, both class A and class B, and example of which is myogenin (Wright et al., 1989, *Cell* 56:607–617); the MADS box-containing transcription factors such as MEF2C (Han et al., 1997, *Nature* 386:296–299); homeodomain-containing factors, an example of which is Drosophila bicoid or any of the factors represented by the four hox gene clusters (Akam, 1987, *Development*, 101:1–22; Burke et al., 1995, *Development*, 121:333–346); Pou domain containing-factors such as Pit-1 (Ingraham et al., 1990, *Annu Rev Physiol*, 52:773–791), factors involved in tumor suppression such as p53 (Levine et al., 1991, *Nature*, 351:453–456; Picksley and Lane, 1994, *Current Opinion in Cell Biology*, 6:853–858); and Rb (Picksley and Lane, 1994, *Current Opinion in Cell Biology* 6:853–858) or any protein shown to play a role in regulation of cell cycle or programmed cell death; other $Zn^{2+}$ finger-containing transcription factors such as Sp1 (Lewin, 1990, *Cell*, 61:1191–1164; Ptashne and Gann, 1990, *Nature*, 346:329–31); steroid binding factors, an example of which is the estrogen receptor (Barnes and Adcock, 1993, *TiPS*, 14:436–441); and leucine zipper transcription factors such as the CCAAT box-binding protein C/EBP (Vinson et al., 1989, *Science*, 246:911–916).

In addition, any of a wide variety of prokaryotic or viral DNA binding proteins, or prokaryotic or viral proteins which interact with the DNA indirectly through protein/protein, protein/RNA or other mechanisms may be incorporated into the subject chimeric virus. These include, but are in no way limited to, the RNA polymerase holoenzyme and/or its subunits; and the auxiliary proteins, an example of which is CRP (Botsford and Harman, 1992, *Microbiol Rev* 56:100–122). Additionally, prokaryotic or eukaryotic viral proteins as well as proteins encoded by transposable or retrotransposable elements shown or thought to interact either directly or indirectly with DNA may be used to practice the present invention. Examples of such proteins include, but are in no way limited to, the lambda bacteriophage repressor protein (Sauer et al., 1990, *Adv Protein Chem*, 40:1–61); the *E. coli* LacI repressor protein (Coulondre and Miller, 1977, *J Mol Biol*, 117:577–606); and the yeast Ty3 retrotransposase (Kirchner et al., 1995, *Science*, 267:1488–1491).

Other specific examples of DNA binding proteins covered by the present invention include, but are in no way limited to, c-myb, AAF, abd-A, Abd-B, ABF-2, ABF1, ACE2, ACF, ADA2, ADA3, Adf-1, Adf-2a, ADR1, AEF-1, AF-2, AFP1, AGIE-BP1, AhR, AIC3, AIC4, AID2, AIIN3, ALF1B, alpha-1, alpha-CP1, alpha-CP2a, alpha-CP2b, alpha-factor, alpha-PAL, alpha2uNF1, alpha2uNF3, alphaA-CRYBP1, alphaH2-alphaH3, alphaMHCBF1, aMEF-2, AML1, AnCF, ANF, ANF-2, Antp, AP-1, AP-2, AP-3, AP-5, APETALA1, APETALA3, AR, ARG RI, ARG RII, Arnt, AS-C T3, AS321, ASF-1, ASH-1, ASH-3b, ASP, AT-13P2, ATBF1-A, ATF, ATF-1, ATF-3, ATF-3deltaZIP, ATF-adelta, ATF-like, Athb-1, Athb-2, Axial, abaA, ABF-1, Ac, ADA-NF1, ADD1, Adf-2b, AF-1, AG, AIC2, AIC5, ALF1A, alpha-CBF, alpha-CP2a, alpha-CP2b, alpha-IRP, alpha2uNF2, alphaH0, AmdR, AMT1, ANF-1, Ap, AP-3, AP-4, APETALA2, aRA, ARG RIII, ARP-1, Ase, ASH-3a, AT-BP1, ATBF1-B, ATF-2, ATF-a, ATF/CREB, Ato, B factor, B", B-Myc, B-TFIID, band I factor, BAP, Bcd, BCFI, Bcl-3, beta-1, BETA1, BETA2, BF-1, BGP1, BmFTZ-F1, BP1, BR-C Z1, BR-C Z2, BR-C Z4, Brachyury, BRF1, BrlA, Brn-3a, Brn-4, Brn-5, BUF1, BUF2, B-Myb, BAF1, BAS1, BCFII, beta-factor, BETA3, BLyF, BP2, BR-C Z3, brahma, byr3, c-abl, c-Ets-1, c-Ets-2, c-Fos, c-Jun, c-Maf, c-myb, c-Myc, c-Qin, c-Rel, C/EBP, C/EBPalpha, C/EBPbeta, C/EBPdelta, C/EBPepsilon, C/EBPgamma, C1, CAC-binding protein, CACCC-binding factor, Cactus, Cad, CAD1, CAP, CArG box-binding protein, CAUP, CBF, CBP, CBTF, CCAAT-binding factor, CCBF, CCF, CCK-1a, CCK-1b, CD28RC, CDC10, Cdc68, CDF, cdk2, CDP, Cdx-1, Cdx-2, Cdx-3, CEBF, CEH-18, CeMyoD, CF1, Cf1a, CF2-I, CF2-II, CF2-III, CFF, CG-1, CHOP-10, Chox-2.7, CIIIB1, Clox, Cnc, CoMP1, core-binding factor, CoS, COUP, COUP-TF, CP1, CPlA, CPlB, CP2, CPBP, CPC1, CPE binding protein CPRF-1, CPRF-2, CPRF-3, CRE-BP1, CRE-BP2, CRE-BP3, CRE-BPa, CreA, CREB, CREB-2, CREBomega, CREMalpha, CREMbeta, CREMdelta, CREMepsilon, CREMgamma, CREMtaualpha, CRF, CSBP-1, CTCF, CTF, CUP2, Cut, Cux, Cx, cyclin A, CYS3, D-MEF2, Da, DAL82, DAP, DAT1, DBF-A, DBF4, DBP, DBSF, dCREB, dDP, dE2F, DEF, Delilah, delta factor, deltaCREB, deltaE1, deltaEF1, deltaMax, DENF, DEP, DF-1, Dfd, dFRA, dioxin receptor, dJRA, D1, DII, Dlx, DM-SSRP1, DMLP1, DP-1, Dpn, Dr1, DRTF, DSC1, DSP1, DSXF, DSXM, DTF, E, E1A, E2, E2BP, E2F, E2F-BF, E2F-I, E4, E47, E4BP4, E4F, E4TF2, E7, E74, E75, EBF, EBF1, EBNA, EBP, EBP40, EC, ECF, ECH, EcR, eE-TF, EF-1A, EF-C, EF1, EFgamma, Egr, eH-TF, EIIa, EivF, EKLF, Elf-1, Elg, Elk-1, ELP, Elt-2, EmBP-1, embryo DNA binding protein, Emc, EMF, Ems, Emx, En, ENH-binding protein, ENKTF-1, epsilonF1, ER, Erg, Esc, ETF, Eve, Evi, Evx, Exd, Ey, f(alpha-epsilon), F-ACT1, f-EBP, F2F, factor 1-3, factor B1, factor B2, factor delta, factor I, FBF-Al, Fbf1, FKBP59, Fkh, F1bD, Flh, Fli-1, FLV-1, Fos-B, Fra-2, FraI, FRG Y1, FRG Y2, FTS, Ftz, Ftz-F1, G factor, G6 factor, GA-BF, GABP, GADD 153, GAF, GAGA factor, GAL4, GAL80, gamma-factor, gammaCAAT, gammaCAC, gammaOBP, GATA-1, GATA-2, GATA-3, GBF, GC1, GCF, GCF, GCN4, GCR1, GE1, GEBF-I, GF1, GFI, Gfi-1, GFII, GHF-5, GL1, Glass, GLO, GM-PBP-1, GP, GR, GRF-1, Gsb, Gsbn, Gsc, Gt, GT-1, Gtx, H, H16, H1lTF1, H2Babp1, H2RIIBP, H2TF1, H4TF-1, HAC1, HAP1, Hb, HBLF, HBP-1, HCM1, heat-induced factor, HEB, HEF-1B, HEF-1T, HEF-4C, HEN1, HES-1, HIF-1, HiNF-A, HIP1, HIV-EP2, Hlf, HMBI, HNF-1, HNF-3, Hox11, HOXA1, HOXA10, HOXA10PL2, HOXA11, HOXA2, HOXA3, HOXA4, HOXA5, HOXA7, HOXA9, HOXB1, HOXB3, HOXB4, HOXB5, HOXB6, HOXB7, HOXB8, HOXB9, HOXC5, HOXC6, HOXC8, HOXD1, HOXD10, HOXD11, HOXD12, HOXD13, HOXD4, HOXD8, HOXD9, HP1 site factor, Hp55, Hp65, HrpF, HSE-binding protein, HSF1, HSF2, HSF24, HSF3, HSF30, HSF8, hsp56, Hsp90, HST, HSTF, I-POU, IBF, IBP-1, ICER, ICP4, ICSBP, Id1, Id2, Id3, Id4, IE1, EBP1, IEFga, IF1, IF2, IFNEX, IgPE-1, IK-1, IkappaB, Il-1 RF, IL-6 RE-BP, Il-6 RF, ILF, ILRF-A, IME1, INO2, INSAF, IPF1, IRBP, IRE-ABP, IREBF-1, IRF-1, ISGF-1, Isl-1, ISRF, ITF, IUF-1, Ixr1, JRF, Jun-D, JunB, JunD, K-2, kappay factor, kBF-A, KBF1, KBF2, KBP-1, KER-1, Ker1, KN1, Kni, Knox3, Kr, kreisler, KRF-1, Krox-20, Krox-24, Ku autoantigen, KUP, Lab, LAC9, LBP, Lc, LCR-F1, LEF-1, LEF-1S, LEU3, LF-A1, LF-B1, LF-C, LF-H3beta, LH-2, Lim-1, Lim-3, lin-11, lin-31, lin-32, LIP, LIT-1, LKLF, Lmx-1, LRF-1, LSF, LSIRF-2, LVa, LVb-binding factor, LVc, LyF-1, Lyl-1, M factor, M-Twist, M1, m3, Mab-18, MAC1, Mad, MAF, MafB, MafF, MafG, MafK, Ma163, MAPF1, MAPF2, MASH-1, MASH-2, mat-Mc, mat-Pc, MATa1, MATalpha1, MATalpha2, MATH-1, MATH-2, Max1, MAZ, MBF-1, MBP-1, MBP-2, MCBF, MCM1, MDBP, MEB-1, Mec-3, MECA, mediating factor, MEF-2, MEF-2C, MEF-2D, MEF1, MEP-1, Meso1, MF3, Mi, MIF, MIG1, MLP, MNB1a, MNF1, MOK-2, MP4, MPBF, MR, MRF4, MSN2, MSN4, Msx-1, Msx-2, MTF-1, mtTF1, muEBP-B, muEBP-C2, MUF1, MUF2, Mxi1, Myef-2, Myf-3, Myf-4, Myf-5, Myf-6, Myn, MyoD, myogenin, MZF-1, N-Myc, N-Oct-2, N-Oct-3, N-Oct-4, N-Oct-5, Nau, NBF, NC1, NeP1, Net, NeuroD, neurogenin, NF III-a, NF-1, NF-4FA, NF-AT, NF-BA1, NF-CLE0a, NF-D, NF-E, NF-E1b, NF-E2, NF-EM5, NF-GMa, NF-H1, NF-IL-2A, NF-InsE1, NF-kappaB, NF-lambda2, NF-MHCIIA, NF-muE1, NF-muNR, NF-S, NF-TNF, NF-U1, NF-W1, NF-X, NF-Y, NF-Zc, NFalphal, NFAT-1, NFbetaA, NFdeltaE3A, NFdeltaE4A, NFe, NFE-6, NFH3-1, NFH3-2, NFH3-3, NFH3-4, NGFI-B, NGFI-C, NHP, Nil-2-a, NIP, NIT2, Nkx-2.5, NLS1, NMH7, NP-III, NP-IV, NP-TCII, NP-Va, NRDI, NRF-1, NRF-2, Nrf1, Nrf2, NRL, NRSF form 1, NTF, NUC-1, Nur77, OBF, OBP, OCA-B, OCSTF, Oct-1, Oct-10, Oct-11, Oct-2, Oct-2.1, Oct-2.3, Oct-4, Oct-5, Oct-6, Oct-7, Oct-8, Oct-9, Oct-B2, Oct-R, Octa-factor, octamer-binding factor, Odd, Olf-1, Opaque-2, Otd, Otx1, Otx2, Ovo, P, P1, p107, p130, p28 modulator, p300, p38erg, p40x, p45, p49erg, p53, p55, p55erg, p58, p65delta, p67, PAB1, PacC, Pap1, Paraxis, Pax-1, Pax-2, Pax-3, Pax-5, Pax-6, Pax-7, Pax-8, Pb, Pbx-1a, Pbx-1b, PC, PC2, PC4, PC5, Pcr1, PCRE1, PCT1, PDM-1, PDM-2, PEA1, PEB1, PEBP2, PEBP5, Pep-1, PF1, PGA4, PHD1, PHO2, PHO4, PHO80, Phox-2, Pit-1, PO-B, pointedP1, Pou2, PPAR, PPUR, PPYR, PR, PR A, Prd, PrDI-BF1, PREB, Prh proein a, protein b, proteinc, protein d, PRP, PSE1, PTF, Pu box binding factor, PU.1, PUB1, PuF, PUF-I, Pur factor, PUT3, pX, qa-1F, QBP, R, R1, R2, RAd-1, RAF, RAP1, RAR, Rb, RBP-Jkappa, RBP60, RC1, RC2, REB1, RelA, RelB, repressor of CAR1 expression, REX-1, RF-Y, RF1, RFX, RGM1, RIM1, RLM1, RME1, Ro, RORalpha, Rox1, RPF1, RPGalpha, RREB-1, RRF1, RSRFC4, runt, RVF, RXR-alpha, RXR-beta, RXR-beta2, RXR-gamma, S-CREM, S-CREMbeta, S8, SAP-1a, SAP1, SBF, Sc, SCBPalpha, SCD1/BP, SCM-inducible factor, Scr, Sd, Sdc-1, SEF-1, SF-1, SF-2, SF-3, SF-A, SGC1, SGF-1, SGF-2, SGF-3, SGF-4, SIF, SIII, Sim, SIN1, Skn-1, SKO1, Slp1, Sn, SNP1, SNF5, SNAPC43, Sox-18, Sox-2, Sox-4, Sox-5, Sox-9, Sox-LZ, Sp1, spE2F, Sph factor, Spi-B, Sprm-1, SRB10, SREBP, SRF, SRY, SSDBP-1, ssDBP-2, SSRP1, STAF-50, STAT, STAT1, STAT2, STAT3, STAT4, STAT5, STAT6, STC, STD1, Ste11, Ste12, Ste4, STM, Su(f), SUM-1, SWI1, SWI4, SWI5, SWI6, SWP, T-Ag, t-Pou2, T3R, TAB, all TAFs including subunits, Tal-1, TAR factor, tat, Tax, TBF1, TBP, TCF, TDEF, TEA1, TEC1, TEF, tel, Tf-LF1, TFE3, all TFII related proteins, TBA1a, TGGCA-binding protein, TGT3, Th1, TIF1, TIN-1, TIP, T11, TMF, TR2, Tra-1, TRAP, TREB-1, TREB-2, TREB-3, TREF1, TREF2, Tsh, TTF-1, TTF-2, Ttk69k, TTP, Ttx, TUBF, Twi, TxREBP, TyBF, UBP-1, Ubx, UCRB, UCRF-L, UF1-H3beta, UFA, UFB, UHF-1, UME6, Unc-86, URF, URSF, URTF, USF, USF2, v-ErbA, v-Ets, v-Fos, v-Jun, v-Maf, v-Myb, v-Myc, v-Qin, v-Rel, Vab-3, vaccinia virus DNA-binding protein, Vav, VBP, VDR, VETF, vHNF-1, VITF, Vmw65, Vp1, Vp16, Whn, WT1, X-box binding protein, X-Twist, X2BP, XBP-1, XBP-2, XBP-3, XF1, XF2, XFD-1, XFD-3, xMEF-2, XPF-1, XrpFI, XW, XX, yan, YB-1, YEB3, YEBP, Yi, YPF1, YY1, ZAP, ZEM1, ZEM2/3, Zen-1, Zen-2, Zeste, ZF1, ZF2, Zfh-1, Zfh-2, Zfp-35, ZID, Zmhoxla, Zta and all related characterized and uncharacterized homologs and family members related to these DNA binding proteins or activities.

Finally, the present invention contemplates the use of virtually any purified DNA binding activity that can be UV, chemically, or enzymatically linked to INT and used to direct site-specific integration.

Previous studies demonstrating engineered site-specific integration have been restricted to in vitro assays. While such studies generally address the possibility that integration may be directed to artificially engineered target regions in vitro, they in no way establish that similar results could be obtained under physiologically relevant conditions in vivo. Moreover, the in vitro studies in no way establish that the integration reaction may be guided to specific naturally occurring sequences present in chromatinized DNA in living cells in vivo. Unlike the in vitro studies, the present invention describes the unique generation and use of mature infectious viral particles that incorporate integrase/DNA binding protein fusions that direct the nonrandom integration into the genomes of living host cells in tissue culture. Additionally, the specifically exemplified chimeric proteins of the present invention are designed to include the nucleosomal protein or transcription factor domains at the C-terminal region or C-terminal end of the INT protein. This arrangement is necessary for incorporation of the modified INT proteins into the mature viral particles that are produced by the appropriate packaging cells. While the presently described INT fusions occur at the C-terminal region of integrase, the present invention is in no way limited to fusion at the exemplified site. Other sequences that may be used to practice the present invention include GenBank accession Nos. J02255-57, M76668, X54156, J04238, and other readily available clones and sequences.

Infection of host cells with the modified integrase/transcription factor fusion proteins, and the subsequent integration of the VICTR series of LTR vectors (described below) into regions proximal to target sequences provides a unique and powerful method for rapid gene identification and disruption.

The presently described invention allows for the biased selection of sites for proviral integration and establishment. Typically, integration occurs in proximity to loci that are regulated by the particular transcription factor used to construct the chimeric INT protein. Alternatively, integration can also be biased using INT chimeras that incorporate protein binding domains in addition to, or in lieu of, the DNA binding domain. Such chimeric INT proteins further bias integration by specifically binding to protein factors that are in turn associated with specific DNA sequences. As such, targeted integration is mediated by an indirect association between the integration complex and the target sequence.

An additional embodiment of the present invention involves the construction of INT chimeras that incorporate highly basic DNA binding proteins. Vectors packaged into infectious virions incorporating these constructs exhibit a significantly increased ability to more broadly access and integrate into the cellular genome.

Although the retrovirus specifically described in the present invention are derived from the Moloney murine leukemia virus, and murine embryonic stem cells are generally used as targets, the present invention is not limited to this particular viral strain or host cell type. For example, the presently described technology may be adapted to a wide variety of both DNA and RNA viral vector systems including, but not limited to, Moloney murine leukemia virus, mouse mammary tumor virus, adeno-associated virus, lentivirus, e.g., simian/human immunodeficiency virus, human T-cell leukemia virus, simian virus (SV40), feline leukemia virus, Friend leukemia virus, bovine leukemia virus, herpesvirus (including Epstein-Barr virus), polyomavirus and papillomavirus. The present technology can also be adapted to both transposable and retrotransposable elements of prokaryotic or eukaryotic origin, examples of which include the bacterial transposons such as Tn5, the yeast Ty retrotransposons and Drosophila P-elements. The presently described invention is in no way limited to the above listed transposable elements.

Similarly, preferred target cells for the present invention include, but are not limited to, cells derived from both human and non human origins including vertebrates and mammals, bovine, ovine, porcine, canine, feline, avian, bony and cartilaginous fish, rodents including mice (Mus musculus) and rats, primates including man (Homo sapiens), and monkeys, ferrets, sheep, rabbits and guinea pigs.

Viral vectors, and particularly retroviral vectors, have been used in a wide variety of gene delivery applications in living animal subjects, including humans, in vivo. In order to specifically investigate patterns of gene expression and gene regulation in vivo, infectious gene trapping virus incorporating suitably constructed to chimeric integrase molecules may be used to infect test living test animals in vivo. The infected tissues may then be rescued from the animals and subject to selective culture. Subsequently, the functional features of the gene trapping vectors may be exploited and used to identify the in vivo expression patterns of the targeted genes. Consequently, in addition to allowing targeted gene discovery in living cells in culture (in vivo, as opposed to purely biochemical reactions, e.g., in vitro), the present invention is also applicable to methods of targeted in discovery in living animals in vivo.

5.2. Mutagenic vectors for use in targeted gene discovery.

Chimeric integrase proteins containing exogenous DNA binding and oligomerization domains can direct targeted integration as well as integration into expanded regions of the cellular genome. However, the design of the vector being integrated, and hence the structure of the resulting provirus, can drastically effect the efficiency of gene discovery and mutagenesis. For example, the fact that enhancer elements containing factor binding sites are known to be present upstream and downstream of exonic sequences as well as within introns, when taken in conjunction with data indicating that splicing may occur over large genomic regions, can drastically complicate gene discovery efforts.

The presently described vectors allow for targeted gene trapping schemes that cumulatively compensate for the full spectrum of position-specific complications. Although a number of investigators have developed gene trapping vectors and procedures for use in mouse and other cells (von Melchner, 1989; Yoshida et al., 1995, *Transgenic Research*, 4:277–287; Allen et al., 1988, *Nature*, 333:852–855; Bellen et al., 1989, *Genes & Development*, 3:1288–1300; Bier et al., 1989, *Genes & Development*, 3:1273–1287; Brenner et al., 1989, *Proc Natl Acad Sci, USA*, 86:5517–5521; Friedrich and Soriano, 1991, *Genes & Development*, 5:1513–1523; Friedrich and Soriano, 1993, *Methods in Enzymology*, 225:681–701; Goff, 1987, *Methods in Enzymology*, 151:489–502; Gossler et al., 1989, *Science* 244:463–65; Hope, 1991, *Development*, 113:399–408; Kerr et al., 1989, *Cold Spring Harbor Symposia on Quantitative Biology*, LIV:767–776; Reddy et al., 1991, *J Virol*, 65:1507–1515; Reddy et al., 1992, *Proc Natl Acad Sci USA*, 89:6721–6725; Skarnes et al., 1992, *Genes & Development*, 6:903–918), none of the above strategies have been applied in the context of directing integration to either specific sites or expanding the accessibility of the host genome to gene trapping. The presently described gene trapping system incorporates a number of significant improvements to the published SA (splice acceptor) DNA vectors, and the ROSA (reverse orientation, splice acceptor) retroviral vectors (Friedrich and Soriano, 1991; Chen and Chasin, 1994, *Molecular and Cellular Biology*, 14 No. 3:2140–2146). For example, the presently described vectors use the selectable markers puromycin N-acetyl transferase, neomycin phosphotransferase and bgeo. The latter markers fuse the B-galactosidase and neomycin phosphotransferase genes to produce a fusion product of the two genes.

Additionally, similar to the ROSA design, some of the presently described vectors incorporate a splice acceptor sequence upstream from the marker gene and a polyadenylation signal sequence downstream from the marker. The markers are integrated after retroviral infection utilizing viruses modified to incorporate chimeric INT proteins, and gene trap events representing transcription factor targets are selected based on resistance to the appropriate antibiotic that results from the activation of Bgeo, puro or neo expression via splicing from the endogenous target gene splice donor sequence to the vector encoded splice acceptor located upstream from the marker. This type of integration disrupts the transcription unit and preferably results in a null mutation at the target locus. It requires endogenous expression of the gene in the cell line being infected as well as a binding site for the transcription factor located either intronically or 3' of the polyadenylation signal. In order to trap genes not expressed in embryonic stem or other cells, the above mentioned selectable markers have been constructed with a constitutively active promoter and splice donor (SD) as described below.

Although gene trapping has proven to be a useful analytical tool, the present invention contemplates gene trapping, or more specifically, the trapping of targets for transcriptional regulation by a particular DNA binding protein. By judicious selection of the technologies incorporated into the present invention, the presently described methods and tools are easily adapted to commercial scale applications. The vectors utilized in the present invention have been engineered to overcome the shortcomings of the early gene trap vector designs, and to facilitate procedures allowing high throughput. In addition, procedures are described that allow the rapid and facile acquisition of sequence information from each trapped target cDNA which may be adapted to allow complete automation. These latter procedures are also designed for flexibility so that additional molecular information can easily be obtained. The present invention therefore incorporates downstream gene identification and simultaneous mutation into a unique tool.

The described gene trapping vectors provide for additional features that are useful in the construction and indexing of the collection of cells. Typically, gene trapping vectors are designed to detect insertions into transcribed gene regions within the genome. They generally consist of a selectable marker whose normal expression is handicapped by exclusion of some element required for proper transcription. When the vector integrates into the genome near the factor binding site, and acquires the necessary element by juxtaposition, expression of the selectable marker is activated. When such activation occurs, the cell can survive when grown in the appropriate selective medium which allows for the subsequent isolation and characterization of the trapped downstream target gene. Integration of the gene trap generally causes the target gene at the site of integration to be mutated thus disrupting wild-type function. Some gene trapping vectors have a splice acceptor preceding a selectable marker and a polyadenylation signal following the selectable marker, and the selectable marker gene has its own initiator ATG (methionine) codon. Using this arrangement, the fusion transcripts produced after integration generally only comprise exons 5' to the insertion site and to the known marker sequences. Where the vector has inserted into the 5' region of the gene, it is often the case that the only exon located 5' to the vector is a non-coding exon. Accordingly, the sequences obtained from such fusions do not provide the desired sequence information about the relevant gene products. This is due to the fact that untranslated sequences are generally less well conserved than coding sequences.

To compensate for the short-comings of earlier vectors, a subset of the vectors of the present invention have been designed so that 3' exons are appended to the fusion transcript by replacing the polyadenylation and transcription termination signals of earlier ROSA vectors with a splice donor (SD) sequence. Consequently, transcription and splicing generally results in a fusion between all or most of the endogenous transcript and the selectable marker exon, for example bgeo, neo or puro. The exon sequences immediately 3, to the selectable marker exon may then be sequenced and used to establish a database of expressed sequence tags representing downstream target genes. The presently described procedures will typically provide about 200 nucleotides of sequence, and often significantly more. These sequences will generally be coding and therefore informative.

Where applicable, the presently described vectors generally incorporate a consensus splice donor sequence. One advantage of using a consensus splice donor is that it often overrides that of the endogenous first exon. Thus, in certain instances, integration events upstream from the first exon still splice effectively into the second exon effectively generating a null mutation. In the context of target gene identification this is essential as enhancer elements generally occur well upstream of the 5' most exon.

Internal exons in mammalian transcripts are generally quite small, on the average 137 bases with few over 300 bases in length. Consequently, a large internal exon may be spliced less efficiently. Thus, the presently described vectors have been designed to sandwich relatively small selectable markers (for example: neo, approximately 800 bases, or a smaller drug resistance gene such as puro, approximately 600 bases, or blasticidin [blast], approximately 400 bases) between the requisite splicing elements to produce relatively small exons. Exons of this size are more typical of mammalian exons and do not unduly hinder cellular splicing. Such design considerations are novel to the presently disclosed gene trapping vectors. Accordingly, an additional embodiment of the claimed vectors is that the respective splice acceptor and splice donor sites are engineered such that they are operatively positioned close to the ends of the selectable marker coding region (the region spanning from the initiation codon to the termination codon). Generally, the splice acceptor or splice donor sequences shall appear within about 80 bases from the nearest end of the coding region, preferably within about 50 bases from the nearest end of the coding region, more preferably within about 30 bases from the nearest end of the coding regions and specifically within about 20 bases of the nearest end of the selectable marker coding region.

Several representative examples of the presently described vectors are shown in retroviral form in FIG. 2. The proviruses shown in the FIG. 2 represent the viral genome after retroviral infection of the target cells and the integration of the viral genome into target cell DNA. These vectors are termed VICTR which is an acronym for "viral constructs for trapping".

The vectors VICTR 1 and 2 are designed to trap transcription factor targets that are transcribed in the target cell. Because these vectors contain a splice acceptor at the 5' end, they require target binding sites to be located 3' of the first exon for appropriate integration and subsequent splicing to occur. To trap target genes that are not expressed in the target cell, gene trap vectors such as VICTR 3, 4 and 5 (described below) are provided. These vectors have been engineered to contain a selectable marker regulated by promoter element that is capable of initiating transcription in virtually any host cell type. However, in order to get proper translation of the marker product, and thus render the cell resistant to the selective antibiotic, a polyadenylation signal and a transcription termination sequence must be provided. Vectors VICTR 3 through 5 are constructed such that an effective polyadenylation signal can only be provided by splicing with an externally provided downstream exon that contains a polyadenylation site. Therefore, since the selectable marker coding region ends only in a splice donor sequence, factor binding sites must be positioned 5' to a polyadenylation signal in order for the selectable marker to be integrated and properly expressed. In essence, these vectors append the foreign exon encoding the marker to the 5' end of an endogenous target transcript. Accordingly, these vectors tag downstream target genes and create mutations that are used to make clones that will become part of a larger library of mutated cells.

The VICTR series of vectors, or similarly designed and constructed vectors, were engineered to address the above design considerations. A more specific description of representative samples of the VICTR vector series is provided below.

VICTR 1 is a terminal exon gene trap. VICTR 1 does not contain a control region that effectively mediates the expression of the selectable marker gene. Instead, the coding region of the selectable marker contained in VICTR 1, in this case encoding puromycin resistance (but which can be any selectable marker functional in the target cell type), is preceded by a splice acceptor sequence and followed by a polyadenylation signal sequence. The coding region of the puro gene has an initiator ATG which is downstream and adjacent to a region of sequence that is most favorable for translation initiation in eukaryotic cells the so called Kozak consensus sequence (Kozak, 1989, *Journal of Cell Biology*, 108:229–241). With a Kozak sequence and an initiator ATG, the puro gene in VICTR 1 is activated by integrating proximal to transcription factor binding sites that are located within an intron or 3' (see below) of an active gene, and the resulting fusion transcript is translated beginning at the puromycin initiation (ATG/AUG) codon. However, terminal gene trap vectors need not incorporate an initiator ATG codon. In such cases, the gene trap event requires splicing and the translation of a fusion protein that is functional for the selectable marker activity. The inserted puromycin coding sequence must therefore be translated in the same frame as the "trapped" downstream target gene.

The splice acceptor sequence used in VICTR 1 and other members of the VICTR series is derived from the adenovirus major late transcript splice site located at the intron 1/exon 2 boundary. For the purposes of the present invention, a sequence has been "derived" from a another sequence when the parent sequence has directly or indirectly been used as a template for the production or engineering (i.e., mutation, deletion, etc.) of the derived sequence. This sequence contains a polypyrimidine stretch preceding the AG dinucleotide which denotes the actual splice site. Such a consensus splice acceptor will, in many instances, override the endogenous splice acceptor sites even when located 3' of the polyadenylation signal. This is critical for the characterization of target genes whose enhancers specific for the studied transcription factor exist 3' of this signal sequence. The presently described vectors contemplate the use of any similarly derived splice acceptor sequence. Preferably, the splice acceptor site will only rarely, if ever, be involved in alternative splicing events.

The polyadenylation signal at the end of the puro gene is derived from the bovine growth hormone gene. Any similarly derived polyadenylation signal sequence could be used if it contains the canonical AATAAA or a similar sequence and can be demonstrated to terminate transcription and cause a polyadenylate tail to be added to the engineered coding exons.

VICTR 2 is a modification of VICTR 1 in which the polyadenylation signal sequence is removed and replaced by a splice donor sequence. Like VICTR 1, VICTR 2 does not contain a control region that effectively mediates the expression of the selectable marker gene. Typically, the splice donor sequence to be employed in a VICTR series vector shall be determined by reference to established literature or by experimentation to identify which sequences properly initiate splicing at the 5' end of introns in the desired target cell. The specifically exemplified sequence, AGGTAAGT, results in splicing occurring in between the two G bases. Downstream genes trapped by VICTR 2 splice upstream exons onto the 5' end of the puro exon and downstream exons onto the 3' end of the puro exon. Accordingly, VICTR 2 effectively mutates gene expression by inserting a foreign exon in-between two naturally occurring exons in a given transcript. The design of VICTR 2 requires an enhancer binding site to be present within intronic sequences of the downstream target for appropriate site-directed integration and ensuing trapping to occur. Again, the puro gene may or may not contain a consensus Kozak translation initiation sequence and properly positioned ATG initiation codon.

As discussed above, downstream gene trapping by VICTR 1 and VICTR 2 requires that the mutated gene is expressed in the target cell line. By incorporating a splice donor into the VICTR traps, transcript sequences 3' of the gene trap insertion can be determined. As described above, these sequences are generally more informative about mutated gene because they are more likely to include coding sequences. This sequence information is gathered according to the procedures described below.

VICTR 3 (FIG. 2), VICTR 4 and VICTR 5 are gene trap vectors that do not require the cellular expression of the endogenous trapped gene. The VICTR vectors 3 through 5 all comprise a promoter element that ensures that transcription of the selectable marker would be found in all cells that have taken up the gene trap DNA. This transcription initiates from a promoter, in this case the promoter element from the mouse phosphoglycerate kinase (PGK) gene. However, since the constructs lack a polyadenylation signal there can be no proper processing of the transcript and therefore no translation. The only means to translate the selectable marker and get a resistant cell clone is by acquiring a polyadenylation signal. Since polyadenylation is known to be concomitant with splicing, a splice donor is provided at the end of the selectable marker. Therefore, the only positive gene trap events using the VICTR vectors 3 through 5 will be those that integrate 5' of a splice acceptor site and the polyadenylation signal such that the marker exon is spliced to downstream exons that are properly polyadenylated. This requires a transcription factor binding site to be located in a position upstream of the polyadenylation signal. Given the fact that VICTRs 3 through 5 contain a constitutively active promoter, target genes mutated with the VICTR vectors 3 through 5 need not be expressed in the target cell, and these gene trap vectors can mutate all genes having at least one intron. The design of VICTR vectors 3 through 5 requires a promoter element that will be active in the target cell type, a selectable marker and a splice donor sequence. Although a specific promoter was used in the described embodiments, it should be understood that appropriate promoters may be selected that are known to be active in a given cell type. Typically, the considerations for selecting the splice donor sequence are identical to those discussed for VICTR 2, supra. VICTR 4 differs from VICTR 3 only by the addition of a small exon upstream from the promoter element of VICTR 4. This exon is intended to stop normal splicing of the mutated target gene. It is possible that insertion of VICTR 3 into an intron might not be mutagenic if the gene can still splice between exons, bypassing the gene trap insertion. The exon in VICTR 4 is constructed from the adenovirus splice acceptor described above and the synthetic splice donor also described above. Stop codons are placed in all three reading frames in the exon, which is about 100 bases long. The stops would truncate the endogenous protein and presumably cause a mutation.

A conceptually similar alternative design uses a terminal exon like that engineered into VICTR 5. Instead of a splice donor, a polyadenylation site is used to terminate transcription and produce a truncated message. Stops in all three reading frames are also provided to truncate the endogenous protein as well as the resulting transcript.

Additionally, sequences that are recognized and utilized by recombinase activities can be incorporated into the vectors to facilitate the subsequent removal of specific regions of DNA sequence. For example, a selectable marker that is integrated into the cellular chromosome may be removed from the chromosome using a given recombinase activity provided that the marker is flanked by suitable recognition sequences. Accordingly, an additional vector that may be used to practice of the present invention is VICTR 20. This vector replaces the terminal exon of VICTR 5 with a splice acceptor located upstream of the Bgeo which can be used for both LacZ staining and antibiotic selection. The fusion consists of its own initiating methionine and internal ribosomal entry site for efficient translation. In addition, the PGK promoter and puromycin-splice donor sequences have been flanked by lox P recombination sites. This allows for the ability to both remove and introduce sequences at the integration site and is of potential value with regard to the manipulation of regions proximal to trapped target genes (Barinaga, Science 265:26–8, 1994). While this particular vector includes lox P recombination sites, the present invention is in no way limited to the use of these specific recombination sites. Others, for example frt, may also be used (Akagi et al., Nucleic Acids Res 25:1766–73, 1997).

Given the fact that expression pattern information can provide insight into the possible functions of genes mutated by the current methods, another LTR vector, VICTR 6, has been constructed in a manner similar to VICTR 5 except that the terminal exon has been replaced with either a gene coding for B-galactosidase (B-gal) or a fusion between B-gal and neomycin phosphotransferase (B-geo), each proceeded by a splice acceptor and followed by a polyadenylation signal. Endogenous gene expression and splicing of these markers into cellular transcripts and translation into fusion proteins will allow for increased mutagenicity as well as the delineation of expression through Lac Z staining.

An additional vector, VICTR 12 (FIG. 2), incorporates two separate selectable markers for the analysis of both integration sites and trapped genes. One selectable marker (e.g. puro) is similar to that for VICTRs 3 through 5 in that it contains a promoter element at its 5' end and a splice donor sequence 3'. This gene cassette is located in the LTRs of the retroviral vector. The other marker (neo) also contains a promoter element but has a polyadenylation signal present at the 3' end of the coding sequence and is positioned between the viral LTRs. Both selectable markers contain an initiator ATG for proper translation. The design of VICTR 12 allows for the assessment of absolute titer as assayed by the number of colonies resistant to antibiotic selection for the constitutively expressed marker possessing a polyadenylation signal. This titer can then be compared to that observed for gene-trapping and stable expression of the resistance marker flanked at its 3' end by a splice donor. These numbers are important for the calculation of gene trapping frequency in the context of both nonspecific binding by retroviral integrase and directed binding by chimeric integrase fusions. In addition, it provides an option to focus on the actual integration sites through infection and selection for the marker containing the polyadenylation signal. This eliminates the need for the fusion protein binding to occur upstream and in the proximity of the target gene. Theoretically, any transcription factor binding sites present within the genome are targets for proximal integration and subsequent antibiotic resistance. Analysis of sequences flanking the LTRs of the retroviral vector should reveal canonical factor binding sites. In addition, by including the promoter/splice donor design of VICTR 3, gene-trapping abilities are retained in VICTR 12.

VICTR A (FIG. 2) is a vector which does not contain gene trapping constructs but rather a selectable marker possessing all of the required entities for constitutive expression including, but not limited to, a promoter element capable of. driving expression in eukaryotic cells and a polyadenylation and transcriptional terminal signal. Similar to VICTR 12, downstream gene trapping is not necessary for successful selection using VICTR A. This vector is intended solely to select for successful integrations and serves as a control for the identification of transcription factor binding sites flanking the integrant as mentioned above.

Finally, VICTR B (FIG. 2) is similar to VICTR A in that it comprises a constitutively expressed selectable marker, but it also contains the bacterial B-lactamase ampicillin resistance selectable marker and a ColE1 origin of replication. These entities allow for the rapid cloning of sequences flanking the long terminal repeats through restriction digestion of genomic DNA from infected cells and ligation to form plasmid molecules which can be rescued by bacterial transformation, and subsequently sequenced (FIG. 5). This vector allows for the rapid analysis of cellular sequences that contain putative binding sites for the transcription factor of interest.

Other vector designs contemplated by the present invention are engineered to include an inducible regulatory elements such as tetracycline, ecdysone, and other steroid-responsive promoters (No et al., Proc Natl Acad Sci USA 93:3345–51, 1996; Furth et al., Proc Natl Acad Sci USA 91:9302–6, 1994). These elements are operatively positioned to allow the inducible control of expression of either the selectable marker or endogenous genes proximal to site of integration. Such inducibility provides a unique tool for the regulation of target gene expression.

All of the gene trap vectors of the VICTR series, with the exception of VICTRs A and B, are designed to form a fusion transcript between vector encoded sequence and the trapped target gene. All of the flanking exons may be sequenced according to the methods described in the following section. To facilitate sequencing, specific sequences are engineered onto the ends of the selectable marker (e.g., puromycin coding region). Examples of such sequences include, but are not limited to unique sequences for priming PCR, and sequences complementary to standard M13 sequencing primers. Additionally, stop codons are added in all three reading frames to ensure that no anomalous fusion proteins are produced. All of the unique 3' primer sequences are immediately followed by a synthetic 9 base pair splice donor sequence. This keeps the size of the exon comprising the selectable marker at a minimum to ensure proper splicing, and positions the amplification and sequencing primers immediately adjacent to the flanking trapped exons to be sequenced as part of the generation of the collection of cells representing mutated transcription factor targets.

Since a cryptic splice donor sequence is found in the inverted LTRs, this cryptic splice donor sequence has been removed from the VICTR vectors by site specific mutagenesis. It was deemed necessary to remove this splice donor so that it would not affect trapping associated splicing events.

When any members of the VICTR series are packaged into infectious virus, the direction of transcription of the selectable marker is opposite to that of the direction of the normal transcription of the retrovirus. The reason for this organization is that the regulatory elements such as the polyadenylation signal, the splice sites and the promoter elements found in the various members of the VICTR series interfere with the transcription of the retroviral genome in the packaging cell line. This potential interference may significantly reduce retroviral titers.

Methods of producing viral packaging cell lines are well known in the art. In particular, U.S. Pat. Nos. 5,449,614 and 4,861,719, herein incorporated by reference teach a variety of retroviral packaging cell lines. Generally, the plasmids containing the packaging functions are split with one encoding the gag and pol genes and a second encoding the env gene product. Packaging lines containing two viral genomes have been described (Bosselman et al., *Molec. Cell. Biol.*, 7(5):1797–1806 (1987); Markowitz et al., *J. Virol.*, 62(4):1120–1124 (1988); Danos and Mulligan, *Proc. Natl. Acad. Sci. (USA)* 85:6460–6464 (1988)) and are desirable because they significantly reduce the chances of generating replication competent retrovirus via recombination between the retroviral vector and the packaging construct. Additionally, the LTRs used in the construction of the presently described packaging cell line are preferably self-inactivating. In particular, the enhancer element is removed from the 3' U3 sequences such that the provirus resulting from infection do not have an enhancer in either LTR.

Another novel feature of the present invention is the production of retroviral packaging cell lines that incorporate chimeric integrase molecules into infectious retrovirus. Preferably, the presently described packaging cell lines have been engineered to produce high titer stocks of substantially helper free, infectious retroviral particles that incorporate chimeric INT and a replication defective viral genome (see FIG. 6) (derived from a retroviral vector). More preferably, the packaging cell lines will produce sufficient virus to result in high titer stocks of virus in the packaging cell culture media. For the purposes of the present invention the term "high titer" shall generally refer to concentrations of infectious virus of at least about $10^5$/ml, more typically at least about $5 \times 10^5$/ml, preferably at least about $10^6$/ml, more preferably at least about $5 \times 10^6$/ml, and specifically at least about $10^7$/ml. Typically, retroviral packaging cells will produce less than about $10^{10}$ virus per ml, and more typically less than about $5 \times 10^9$ virus per ml. However, one must further consider that methods for concentrating animal virus preparations are generally known in the art (Graham and Prevec, 1991, *Methods Mol. Biol.*, 7:109–128) and have been used to prepare stocks of infectious virus (albeit adenovirus) with titers of about $10^{13}$/ml.

Although specific gene trapping vectors have been discussed at length above, both alone and in the context of site-specific integration, the invention is by no means to be limited to such vectors. Several different types of vectors that may also be used to incorporate relatively small engineered exons into a target cell transcripts including, but are not limited to, adenovirus vectors, adeno-associated virus vectors, SV40 based vectors, and papilloma virus vectors. Additionally, DNA vectors may be directly transferred into the target cells using any of a variety of chemical or physical means such as lipofection, chemical transfection, electroporation and the like either in combination with or separate from vectors encoding integrase/DNA binding protein fusions. Moreover, mutagenic gene trap vector DNA corresponding to the described VICTR vectors may be introduced into the target cell genome by various transfection techniques which are familiar to those skilled in the art such as electroporation, lipofection, or calcium phosphate precipitation. However, these techniques require the presence of either a chimeric INT fusion protein to mediate the targeted integration or enhanced genome availability. The chimeric INT protein may be introduced into the target cell by any practical means such as, but not limited to, electroporation or calcium phosphate precipitation of constructs encoding the protein or by lipofection or direct injection of previously purified forms of the protein. Examples of such techniques may be found in Sambrook et al. (1989) Molecular Cloning Vols. I–III, Cold Spring Harbor Laboratory Press, Cold Spring Harbor, N.Y., and Current Protocols in Molecular Biology (1989) John Wiley & Sons, all Vols. and periodic updates thereof, herein incorporated by reference. The transfected version of the retroviral vectors and vectors expressing the fusion proteins are typically plasmid DNA molecules containing DNA cassettes comprising the described features.

Other methods related to the described technology include, but are not limited to, methods utilizing retrotransposon and/or retrotransposable elements in the capacity of targeted integration (Morgan et al., Proc Natl Acad Sci USA 93:2801–6, 1996; Chakraborty et al., FASEB J 7:971–7, 1993). Theoretically, one may be able to direct integration of these sequences, which may or may not include the above-described gene-trapping construct, utilizing modified integrase/DNA binding protein fusions of viral or transposon origin. The present invention additionally contemplates effecting targeted integration by providing sequences encoding chimeric integrase either within the transposon or transposable elements, or on separate plasmids or vectors.

The presently described chimeric integrase molecules and the gene trapping methodologies define a novel system for the rapid identification and mutation of genes located in proximity to the DNA binding site of virtually any DNA binding protein. The disruptions in the targeted genes in individual cells can be catalogued and organized into a database of mutation and sequence information. Such databases are ultimately organized into collections of cells containing mutations in each target. Individual mutants and sequence information representing essentially every regulatory target for the transcription factor being studied can subsequently be retrieved from the collection of cells.

The obtained sequence information also provides a ready source of probes that may be used to isolate the full-length gene or cDNA from the host cell, or as heterologous probes for the isolation of homologous target genes in other species. Preferably, such homologues will bind the heterologous probes under highly stringent conditions, such as, for example, hybridization to filter-bound DNA in 0.5 M NaHPO$_4$, 7% sodium dodecyl sulfate (SDS), 1 mM EDTA at 65° C., and washing in 0.1× SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), or possibly under less stringent conditions, such as, for example, moderately stringent conditions, e.g., washing in 0.2× SSC/0.1% SDS at 42° C. (Ausubel et al., 1989, supra).

Genetic mutations often correlate with disease (e.g., breast cancer, Parkinson's, obesity, ataxia telangiectasia, etc.). Given that the present invention allows for directed gene discovery, additional embodiments of the present invention include methods for identifying the genetic basis of disease. For example, genetic mutations can often contribute to the disease state by altering the normal regulatory processes of the cell. As such, once a given transcription factor or regulatory protein has been associated with a given disease, the entire protein, or a relevant domain therefrom, may be incorporated into a chimeric INT and used to identify genes directly or indirectly regulated by the protein. Consequently, the present invention may be used to identify the various proteins involved in a given disease or disease pathway. Diseases of particular interest include, but are not limited to: autoimmune disease, systemic lupus erythematosus, rheumatoid arthritis, inflammatory response, post-angioplasty vascular inflammatory response, bacterial or viral infection, inflammatory bowel disease, diabetes, multiple sclerosis, cancer, asthma, muscular dystrophy, Alzheimer's disease, dementia and other neuropathologies, hypertension, hemochromatosis, porphyrias, galactosemia, hyperlipoproteinemia, gout, interstitial lung disease, platelet disorders, myasthenia gravis, congenital heart disease, cystic fibrosis, and obesity.

Cancers that may be diagnosed or treated using the presently described methods include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors; Nervous system: skyll (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; Breast: carcinoma and sarcoma, and Adrenal glands: neuroblastoma.

In addition to disease, the presently described methods and libraries are equally will suited for identifying the molecular basis for genetically determined advantages such as prolonged life-span, low cholesterol, low blood pressure, cancer, diabetes, obesity, attenuation of severity or prevention of all inflammatory disorders, including, but not limited to coronary artery disease, multiple sclerosis, rheumatoid arthritis, systemic lupus erythematosus, and inflammatory bowel disease.

Viral vectors have long been used to deliver genes to animals, including humans, and animal cells. In particular, engineered retrovirus have been used in a wide variety of in vitro and in vivo gene delivery applications. Given the widespread use of retroviral vectors, it is clear that the presently described methods of directing viral integration to specific target sequences will materially enhance retrovirally mediated gene delivery or gene disruption. Consequently, yet another embodiment of the present invention are methods and tools for effecting both ex vivo and in vivo gene therapy. U.S. Pat. No. 5,399,346 to Anderson et al. is herein incorporated by reference as teaching methods of practicing ex vivo gene therapy in humans. For the purposes of this Application, the terms "treatment", "therapeutic use", or "medicinal use" used herein shall refer to any and all uses which remedy a disease state or symptoms, or otherwise prevent, hinder, retard, or reverse the progression of disease or other undesirable symptoms in any way whatsoever.

Gene therapy usually involves the delivery of one or more genes to a target cells which subsequently express the delivered genes. Expression can be transient, stable, or regulatable (using appropriate promoter elements). When expressed, the product encoded by the delivered gene will directly or indirectly provide the desired benefit to cell or individual being treated.

Although gene delivery often involves enhancing the amount of the delivered gene/protein in the target cell, the presently described methods and tools can be used to reduce the amount of endogenous gene expression in a cell or animal by insertionally inactivating or "knocking out" the targeted gene or its promoter. In addition, the presently described virus can deliver antiviral compounds (such as suicide genes under the tight control of viral specific, e.g., HIV, promoters) while simultaneously targeting integrated proviruses for insertional inactivation.

Additionally, the presently described methods of biasing integration can also be used to significantly enhance the efficiency of gene replacement methods via targeted homologous recombination. (e.g., see Smithies et al., 1985, *Nature,* 317:230–234; Thomas & Capecchi, 1987, *Cell,* 51:503–512; Thompson et al., 1989, *Cell,* 5:313–321; each of which is incorporated by reference herein in its entirety). For example, mutant, or non-functional genes, flanked by DNA homologous to the endogenous target gene (e.g., the coding regions or regulatory regions flanking the target gene) can be used, with or without a selectable marker and/or a negative selectable marker, to transfect cells encoding the undesirable form of the target gene in vivo. Insertion of the DNA construct, via targeted homologous recombination, results in inactivation of the endogenous gene. In fact, the presently described methods of targeted integration can be used to inactivate entire families of genes that are directly or indirectly regulated by a given DNA binding activity, transcription factor, or accessory protein.

Approaches like those mentioned above are particularly well suited to the agricultural field where modifications to ES (embryonic stem) cells can be used to generate animal offspring with specifically manipulated genotypes and phenotypes (e.g., see Thomas & Capecchi 1987 and Thompson 1989, supra). However this approach can also be adapted for use in humans provided that the recombinant DNA constructs are directly administered or targeted to the required site in vivo using the appropriate viral vectors.

Alternatively, endogenous gene expression by target cells can be reduced by targeting deoxyribonucleotide sequences complementary to the regulatory region of the endogenous genes (i.e., the promoter and/or enhancer regions) to form triple helical structures that prevent transcription of the target genes in target cells in the body. (See generally, Helene, 1991, *Anticancer Drug Des.,* 6(6):569–84; Helene et al., 1992, Ann, *N.Y. Acad. Sci.,* 660:27–36; and Maher, 1992, *Bioassays,* 14(12):807–15).

In yet another embodiment of the present invention, the activity of a given product can be reduced using a "dominant negative" approach to effect gene therapy. To this end, constructs that encode defective forms of target genes can be used in gene therapy approaches to diminish the activity of the native products in appropriate target cells by, for example, competing away an activating ligand.

The presently described methods for targeting viral integration allow for a rational approach to elucidating the genetic and regulatory pathways in the cell. As such, additional embodiments of the present invention include assays that identify compounds which bind to regulatory sequences (e.g., promoter sequences) that modulate gene expression. See e.g., Platt, K. A., 1994, *J Biol Chem,* 269:28558–28562, which is incorporated herein by reference in its entirety.

Given that altered cellular phenotypes may be associated with the presently described methods of targeted viral integration, additional aspects of the invention are the use of screening assays to detect altered cellular phenotypes. The following assays are designed to identify compounds that interact with (e.g., bind to) extracellular or intracellular proteins. The compounds which may be screened in accordance with the invention include but are not limited to peptides, antibodies and fragments thereof, prostaglandins, lipids and other organic compounds (e.g., terpines, peptidomimetics) that bind to or mimic the activity triggered by the natural ligand (i.e., agonists) or inhibit the activity triggered by the natural ligand (i.e., antagonists); as well as peptides, antibodies or fragments thereof, and other organic compounds that mimic the natural ligand for a given receptor or signal transduction protein.

Such compounds may include, but are not limited to, peptides such as, for example, soluble peptides, including but not limited to members of random peptide libraries (see, e.g., Lam, K. S. et al., 1991, *Nature,* 354:82–84; Houghten, R. et al., 1991, *Nature,* 354:84–86), and combinatorial chemistry-derived molecular library peptides made of D- and/or L-configuration amino acids, phosphopeptides (including, but not limited to members of random or partially degenerate, directed phosphopeptide libraries; see, e.g., Songyang, Z. et al., 1993, *Cell,* 72:767–778); antibodies (including, but not limited to, polyclonal, monoclonal, humanized, anti-idiotypic, chimeric or single chain antibodies, and FAb, F(ab)$_2$ and FAb expression library fragments, and epitope-binding fragments thereof); and small organic or inorganic molecules.

Other compounds which can be screened in accordance with the invention include but are not limited to small organic molecules that are able to gain entry into an appropriate cell and affect the expression of a gene (e.g., by interacting with the regulatory region or transcription factors involved in gene expression); or such compounds that affect the activity of a gene by inhibiting or enhancing the binding of accessory molecules).

Computer modeling and searching technologies permit identification of compounds, or the improvement of already identified compounds, that can modulate the expression or activity of a given gene. Having identified such a compound or composition, the active sites or regions are identified. Such active sites might typically be the binding partner sites, such as, for example, the interaction domains of a protein with its cognate ligand. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination thereof, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. The compounds found from such a search generally identify modulating compounds, or genes encoding the same, that are selected for further study or gene targeting.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of regulatory protein interactions, and related transduction factors will be apparent to those of skill in the art.

Representative examples of molecular modeling systems include the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

Although described above with reference to design and generation of compounds which could alter binding, one could also screen libraries of known compounds, including natural products or synthetic chemicals, and biologically active materials, including proteins, for compounds which are inhibitors or activators of the proteins and genes being studied using the presently described tools and methods.

Compounds identified via assays such as those described herein may be useful, for example, in treating conditions associated with the under or over production of steroid hormones. Assays for testing the effectiveness of compounds are discussed below.

In vitro systems may be designed to identify compounds capable of interacting with (e.g., binding to) the regulatory proteins identified using the subject methods. The identified compounds may be useful, for example, in modulating the activity of wild type and/or mutant gene products. In vitro systems may also be utilized to screen for compounds that disrupt normal regulatory interactions.

The assays used to identify compounds that bind to regulatory proteins involve preparing a reaction mixture of a given protein and the test compound under conditions and for a time sufficient to allow the two components to interact and bind, thus forming a complex which can be removed and/or detected in the reaction mixture. The protein used can vary depending upon the goal of the screening assay. For example, where agonists of the natural ligand are sought, a full length protein, or a fusion protein containing a protein or polypeptide that affords advantages in the assay system (e.g., labeling, isolation of the resulting complex, etc.) can be utilized.

The screening assays can be conducted in a variety of ways. For example, one method to conduct such an assay would involve anchoring the protein, polypeptide, peptide or fusion protein or the test substance onto a solid phase and detecting binding between the protein and test compound. In one embodiment of such a method, the receptor protein reactant may be anchored onto a solid surface, and the test compound, which is not anchored, may be labeled, either directly or indirectly. In another embodiment of the method, the test protein is anchored on the solid phase and is complexed labeled antibody (and where a monoclonal antibody is used, it is preferably specific for a given region of the protein). Then, a test compound could be assayed for its ability to disrupt the association of the protein/antibody complex.

In practice, microtiter plates, or any modernized iteration thereof, may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the test protein, polypeptide, peptide or fusion protein, or the test compound to anchor any complexes formed in solution, and a labeled antibody specific for the other component of the possible complex to detect anchored complexes.

Macromolecules that interact with a given regulatory or test protein are referred to, for purposes of this discussion, as "binding partners". Therefore, it is desirable to identify compounds that interfere with or disrupt the interaction with such binding partners which may be useful in regulating the gene activity.

The basic principle of the assay systems used to identify compounds that interfere with the interaction between the a protein and its binding partner or partners involves preparing a reaction mixture containing the test protein, polypeptide, peptide or fusion protein as described above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the test protein and its binding partner. Control reaction mixtures are incubated without the test compound or with a placebo. The formation of any complexes between the test protein and the binding partner is then detected. The formation of a complex in the control reaction, but not in the reaction mixture containing the test compound, indicates that the compound interferes with the interaction of the test protein and the binding partner.

The assay for compounds that interfere with protein binding can be conducted in a heterogeneous or homogeneous format. Heterogeneous assays involve anchoring either the test protein or the binding partner onto a solid phase and detecting complexes anchored on the solid phase at the end of the reaction. In homogeneous assays, the entire reaction is carried out in a liquid phase. The examples below describe similar assays which may be easily modified to screen for compounds which disrupt or enhance the interaction. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the test protein and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the test protein, or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the test protein or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the test protein and the interactive binding partner is prepared in which either protein is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt the binding interaction can be identified.

For example of a typical labeling procedure, a test protein or a peptide fragment, e.g., corresponding to the relevant binding domain, can be fused to a glutathione-S-transferase (GST) gene using a fusion vector, such as pGEX-5X-1, in such a manner that its binding activity is maintained in the resulting fusion protein. The interactive binding partner can be labeled with radioactive isotope, for example, by methods routinely practiced in the art. In a heterogeneous assay, e.g., the GST-fusion protein can be anchored to glutathione-agarose beads. The interactive binding partner can then be added in the presence or absence of the test compound in a manner that allows interaction and binding to occur. At the end of the reaction period, unbound material can be washed away. The interaction between the fusion product and the labeled interactive binding partner can be detected by measuring the amount of radioactivity that remains associated with the glutathione-agarose beads. The successful inhibition of binding by the test compound will result in a decrease in measured radioactivity.

Alternatively, the GST-fusion protein and the labeled interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of binding inhibition can be measured by determining the amount of radioactivity associated with the beads.

In another embodiment of the invention, these same techniques can be employed using peptide fragments that correspond to the binding domains of the test proteins, in place of the full length proteins. Any number of methods routinely practiced in the art can be used to identify and isolate the binding sites. These methods include, but are not limited to, mutagenesis of the gene encoding the protein and screening for disruption of binding in a co-immunoprecipitation assay. Sequence analysis of the gene encoding the protein will reveal the mutations that correspond to the region of the protein involved in interactive binding.

The invention encompasses cell-based and animal model-based assays for the identification of compounds exhibiting the ability to alter or correct phenotypes associated with the various genotypes identified and constructed using the present methods. Such cell-based assays can also be used as the standard to assay for purity and potency of the compounds, including recombinantly or synthetically produced proteins or compounds.

Cell-based systems can also be used to identify assess the amount of altered gene expression in a living cell. One tool of particular interest for such assays is green fluorescent protein which is described, inter alia, in U.S. Pat. No. 5,625,048, herein incorporated by reference. Cells that may be used in such cellular assays include, but are not limited to, leukocytes, or cell lines derived from leukocytes, lymphocytes, stem cells, including embryonic stem cells, and the like. In addition, expression host cells (e.g., B95 cells, COS cells, CHO cells, OMK cells, fibroblasts, Sf9 cells) genetically engineered to express a functional proteins of interest and to respond to activation by the natural ligand, as measured by a chemical or phenotypic change, or induction of another host cell gene, can be used as an end point in the assay.

In utilizing such cell systems, cells may be exposed to a compound suspected of exhibiting an ability to affect target gene expression or activation, at a sufficient concentration and for a time sufficient to elicit such an effect in the exposed cells. After exposure, the cells can be assayed to measure alterations in the expression of the desired gene, e.g., by assaying cell lysates for the amount of relevant mRNA transcript (e.g., by Northern analysis), or by directly assaying the amount of a particular protein expressed in the cell. Using such methodology compounds that regulate or modulate expression of the gene of interest are identified as valuable candidates for therapeutic development. Alternatively, the cells are examined to determine whether one or more cellular phenotypes have been altered to resemble a more normal or a more wild type phenotype, or a phenotype more likely to produce a lower incidence or response to a given stimulus.

In addition, animal-based systems, which may include, for example, mice, may be used to identify compounds having a given activity. For example, there are a number of model systems which comprise "knockdown" mice expressing reduced levels of various receptors. In addition, there are a number of mouse models of targeted overexpression of receptors. Such animal models may be used as test systems for the identification of drugs, pharmaceuticals, therapies and interventions which may be effective in treating such disorders.

As an example, animal models may be exposed to a compound suspected of exhibiting an ability to interfere with the a given receptor, or regulatory cascade. The response of the animals to the compound may be monitored by assessing the extent of change, or even reversal, of the engineered phenotype. With regard to intervention, any treatments which reverse any aspect of a given phenotype in vivo should be considered as candidates for further development or potential use in humans. Dosages of test agents may be determined by deriving dose-response curves using methods well known in the art.

An additional invention contemplated by the present invention is a non-human transgenic animal that has been engineered using an infectious virus incorporating a chimeric integrase molecule, or physically incorporates and expresses a gene encoding a chimeric integrase molecule. Such an animal serves as an in vivo target for gene trapping using DNA vectors delivered in vivo (by chemical or electrical means). Additionally, such animals are a source of tissues and cells for further gene trapping studies using cultured cells. Animals suitable for these studies include, but are not limited to, vertebrates, amphibians, fish, birds, mammals, rodents, primates, monkeys, mice, rats, ferrets, dogs, cats, swine, cows and sheep.

Although the use of specific selectable markers have been disclosed and discussed herein, the present invention is in no way limited to the specifically disclosed markers. Additional markers (and associated antibiotics) that are suitable for either positive or negative selection of eukaryotic cells are disclosed, inter alia, in Sambrook et al. (1989) Molecular Cloning Vols. I–III, Cold Spring Harbor Laboratory Press, Cold Spring Harbor, N.Y., and Current Protocols in Molecular Biology (1989) John Wiley & Sons, all Vols. and periodic updates thereof, as well as Table I of U.S. Pat. No. 5,464,764 issued Nov. 7, 1995, the entirety of which is herein incorporated by reference. Any of the disclosed markers, as well as others known in the art, may be used to practice the present invention.

5.3 The Analysis of Mutated Target Genes and Transcripts.

The presently described invention allows for large-scale genetic analysis, i.e., the identification and mutation of transcription factor targets as well as target regions for other DNA binding proteins, of any organism for which there exists culture cell lines. Suitable organisms include, but are not limited to, both human and non human origins including vertebrates and mammals, bovine, ovine, porcine, canine, feline, avian, fish, rodents including mice (Mus musculus) and rats, primates including man (Homo sapiens), and monkeys, ferrets, sheep, rabbits and guinea pigs.

A library or collection of gene trapped cells may be constructed from any type of cell that can be transfected by standard techniques or infected with recombinant retroviral vectors. Where, for example, mouse ES cells are used, the collection of cells constitutes a genetic tool that preferably represents a comprehensive set of mutations in essentially every downstream target gene or sequence for the DNA binding protein used to construct the chimeric integrase molecule. Since ES cells can be injected back into blastocysts and become incorporated into transgenic animals, and ultimately the germ line, the cells in a gene trapped ES cell effectively represent a panel of mutant transgenic mouse strains. The collection of mutated genes in a specific panel generally vary depending upon the particular transcription factor being exploited (see generally, U.S. Pat. No. 5,464,764 issued Nov. 7, 1995, herein incorporated by reference).

Similar methods allow for the construction of virtually any non-human transgenic animal (or animal capable of being rendered transgenic). Such non-human transgenic animals may include, for example, vertebrates, fish, transgenic pigs, transgenic rats, transgenic rabbits, transgenic cattle, transgenic goats and other transgenic animal species, particularly mammalian species, known in the art. Additionally, bovine, ovine, porcine species, other members of the rodent family, e.g. rat, as well as rabbit and guinea pig and non-human primates, such as chimpanzee, may be used to practice the present invention.

Transgenic animals produced using the presently described collection of cells and/or vectors are useful for the study of basic biological processes and diseases including, but not limited to, aging, cancer, autoimmune disease, immune disorders, alopecia, glandular disorder, inflammatory disorders, diabetes, arthritis, high blood pressure, atherosclerosis, cardiovascular disease, pulmonary disease, degenerative diseases of the neural or skeletal systems, Alzheimer's disease, Parkinson's disease, asthma, developmental disorders or abnormalities, infertility, epithelial ulcerations, and microbial pathogenesis (a relatively comprehensive review of such pathogens is provided, inter alia, in Mandell et al., 1990, "Principles and Practice of Infectious Disease" 3rd. ed., Churchill Livingstone Inc., New York, N.Y. 10036, herein incorporated by reference).

By defining the target genes regulated by a particular DNA binding protein, to the extent that a given DNA binding activity may be associated with a given disease important genetic correlations and regulatory cascades may be rapidly elucidated and potential therapies uncovered.

5.4. Generating a Collection of Individually Mutated Cell Clones.

The vectors described in the previous sections, including those encoding modified retroviral integrase/DNA binding protein fusions, are used to infect (or transfect) cells in culture, for example, mouse embryonic stem (ES) cells. Those insertions for which a target gene is trapped as described are identified by being resistant to the antibiotic (e.g., puromycin) which has been added to the culture. Individual clones (colonies) are moved from a culture dish to individual wells of a multi-welled tissue culture plate (e.g. one with 96 wells). From this platform, the clones possessing mutated DNA binding protein targets may be duplicated for storage and subsequent analysis. Each multi-well plate of clones is then processed by molecular biological techniques described in the following section in order to derive the sequence of the target gene that has been mutated. This entire process is presented schematically in FIG. 4 (described below).

5.5. Identifying and Sequencing the Tagged Target Genes in the Collection of Cells.

The relevant nucleic acid sequence data (and derived amino acid sequence information) are obtained using PCR-based techniques that take advantage of the known portion of the fusion transcript sequence (Frohman et al., 1988, *Proc Natl Acad Sci USA,* 1988:8998–9002). Typically, such sequence shall be encoded by the foreign exon containing the selectable marker. The procedure is represented schematically in FIG. 3. Although each step of the procedure may be done manually, the procedure may also be carried out using robots that can deliver reagents to multi-well culture plates (e.g., 96-well plates).

The first step of the process generates single stranded complementary DNA which is used in the 1PCR amplification reaction (FIG. 3). The RNA substrate for cDNA synthesis may either be total cellular RNA or an mRNA fraction; preferably the latter. mRNA is isolated from cells directly in the wells of the tissue culture dish. The cells are lysed and mRNA is bound by the complementary binding of the polyadenylate tail to a solid matrix-bound polythymidine. The bound mRNA is washed several times and the reagents for the reverse transcription (RT) reaction are added. cDNA synthesis in the RT reaction is initiated at random positions along the message by the binding of a random sequence primer (RS). This RS primer has 6–9 random nucleotides at the 3' end to bind sites in the mRNA to prime cDNA synthesis, and a 5' tail sequence of known composition to act as an anchor for PCR amplification in the next step. There is therefore no specificity for the trapped message in the RT step. Alternatively, a poly-dT primer appended to the specific sequences for the PCR may be used. Synthesis of the first strand of the cDNA would then initiate at: the end of each trapped gene. At this point in the procedure, the bound mRNA may be stored (at between about –70° C. and about 4° C.) and reused multiple times. Such storage is a valuable feature where one subsequently desires to analyze individual clones in more detail. The bound mRNA may also be used to clone the entire transcript using any of a variety PCR-based protocols. The technique of PCR is described in numerous publications, including, *PCR: A Practical Approach,* M. J. McPherson et al., IRL Press (1991), PCR Protocols: *A Guide to Methods and Applications,* by Innis et al., Academic Press (1990), and *PCR Technology: Principals and Applications of DNA Amplification,* H. A. Erlich, Stockton Press (1989). PCR is also described in many U.S. patents, including U.S. Pat. Nos. 4,683,195, 4,683,202; 4,800,159; 4,965,188; 4,889,818; 5,075,216; 5,079,352; 5,104,792, 5,023,171; 5,091,310; and 5,066,584, which are hereby incorporated by reference.

Specificity for the trapped fusion transcript is introduced in the next step, PCR amplification. The primers for this reaction are complementary to the anchor sequence of the RS primer and to the selectable marker. Double stranded fragments between a fixed point in the selectable marker gene and various points downstream in the appended transcript sequence are amplified. It is these fragments that subsequently become substrates for DNA sequencing reactions. The various end-points along the transcript sequence are determined by the binding of the random primer during the RT reaction. These PCR products are diluted into the sequencing reaction mix, denatured, and sequenced using a primer specific for the splice donor sequences of the gene trap exon. Although, standard radioactively labeled nucleotides may be used in the sequencing reactions, sequences will typically be determined using standard dye-terminator sequencing in conjunction with automated sequencers (e.g. ABI sequencers and the like).

Several fragments of various sizes may serve as substrates for the sequencing reactions. This is not a problem since the sequencing reaction proceeds from a fixed point as defined by a specific primer sequence. Typically, approximately 200 nucleotides of sequence are obtained for each trapped transcript. Sequences further 3' are then covered by the longer fragments amplified during PCR. A potential problem is created by the anchor sequences 'S' derived from the RS primer. When these sequences are encountered during sequencing of smaller fragments, they register as anomalous dye signals on the sequencing gels. To circumvent this potential problem, a restriction enzyme recognition site is included in the S sequence. Digestion of the double stranded PCR products with this enzyme prior to sequencing eliminates the heterologous S sequences.

5.6. Identifying the Tagged Target Genes by Chromosomal Location.

Any individually tagged target gene may also be identified by PCR using chromosomal DNA as the template. To find an individual clone of interest in the collection of cells described above, genomic DNA is isolated from the pooled clones of ES cells. One primer for the PCR is anchored in the gene trap vector, e.g., a puro exon-specific oligonucleotide. The other primer is located in the genomic DNA of interest. This genomic DNA primer may consist of either (1) DNA sequence that corresponds to the coding region of the gene of interest, or (2) DNA sequence from the locus of the gene of interest. In the first case, the only way that the two primers may be juxtaposed to give a positive PCR result (e.g., the correct size double-stranded DNA product) is if the gene trap vector has inserted into the gene of interest. Additionally, degenerate primers may be used, to identify and isolate related genes of interest. In the second case, the only way that the two primers used may be juxtaposed to provide the desired PCR result is if the gene trap vector has inserted into the region of interest that contains the primer for the known marker.

For example, if one wishes to obtain ES cell clones from the collection of cells that contain mutated target genes located in a certain chromosomal position, PCR primers are designed that correspond to the puro gene (the puro-anchored primer) and a primer that corresponds to a marker known to be located in the region of interest. Several different combinations of marker primers and primers that are located in the region of interest may also be used to obtain optimum results. In this manner, the mutated genes are identified by virtue of their location relative to sets of known markers. DNA binding protein target genes or sequences in a particular chromosomal region of interest could therefore be identified and mutated. The marker primers could also be designed to correspond to sequences of known genes in order to screen for mutations in particular genes by PCR on genomic DNA templates. While this method is likely to be less informative than the RT-PCR strategy, this technique would be useful as an alternative strategy to identify mutations in known genes. In addition, primers that correspond to the sequence of known genes could be used in PCR reactions with marker-specific primers in order to identify ES cell clones that contain mutations in genes proximal to the known genes. Primers may also be designed that correspond to transcription factor binding sites and used in combination with marker specific primers to locate enhancer elements proximal to integration events. The sensitivity of detection is adequate to find such events when positive cDNA clones are subsequently identified as described below in the RT-PCR strategy.

5.7. A Sequence Database that Identifies Target Genes Mutated in the Collection of Cells.

Using the procedures described above, approximately 200 to about 600 bases of sequence from the cellular exons appended to the selectable marker exon (e.g. puro exon in VICTR vectors) may be identified. These sequences provide a means to identify and catalogue the transcription factor target genes mutated in each clone of the library of mutated target cells. Such a database provides both an index for the presently disclosed libraries, and a resource for discovering novel genes regulated by the transcription factor being studied. Alternatively, various comparisons can be made between the database of sequences collected and any other sequence database as would be familiar to those practiced in the art. Additionally, identified sequences that flank integration sites may be catalogued and compared to known promoter/enhancer databases.

The library of specifically targeted mutant cells provides the unique capability for a person to search the database generated from the library for a target for transcriptional regulation by a particular factor based upon some knowledge of the target gene nucleic acid or amino acid sequence. Once a coding sequence is identified, the specific clone in the collection of cells can be accessed and used to study gene function. This is accomplished by studying the effects of the mutation both in vitro and in vivo. For example, cell culture systems and animal models (i.e., transgenic animals) may be generated from the cells in the library using technology familiar to those skilled in the art.

Additionally, the coding sequence information may be used to generate a highly specific probe for isolating both genomic clones from existing databases, as well as a full length cDNA. As well, the probe may be used to isolate the homologous gene from sufficiently related species, including humans. Once isolated, the gene may be over-expressed, or used to generate a targeted knock-out vector that may be used to generate cells and animals that are homozygous for the mutation of interest. Such animals and cells are deemed to be particularly useful as disease models (i.e., cancer, genetic abnormalities, AIDS, etc.), for developmental study, to assay for toxin susceptibility or the efficacy of therapeutic agents, and as hosts for gene delivery and therapy experiments (e.g. experiments designed to correct a specific genetic defect in vivo).

The examples below are solely provided to illustrate the subject invention. Given the level of skill in the art, one may be expected to modify any of the above or following disclosure to produce insubstantial differences from the specifically described features of the present invention. As such, the following examples are provided by way of illustration and should not be construed as limiting the invention in any way whatsoever.

6.0. EXAMPLES 6.1. Demonstration of Infection with Mutant Integrase-Containing Viral Particles.

Previous data on site-directed integration in vitro suggest that the desired integration events are extremely inefficient in comparison to background random integration, a major hurdle that would have to be overcome to observe site-directed integration in vivo (Goulaouic and Chow, 1996, *Journal of Virology* 70, No. 1:37–46, Bushman, 1994, *Proc Natl Acad Sci USA* 91:9233–9237, Katz et al., 1996, *Virology* 217:178–190). The inefficiency is thought to be due to the crippled state of the truncated or fusion-modified integrase. It was postulated that exceptionally high absolute titers (actual viral particle number) would be required for the mutant integrase-containing viruses in order to observe actual site-directed integration events in vivo. Therefore, a strategy was designed to establish packaging cells which optimized for the ability of the cells to produce high numbers of infection-competent viral particles containing the aforementioned mutant integrase constructs and gene trapping vectors. This strategy is outlined in FIG. 6. Briefly, wild-type 3T3 fibroblasts were transfected using a BioRad Genepulser apparatus with a linearized construct digested with ScaI encoding hygromycin resistance and the viral ENV gene under a constitutive promoter. Cells were selected in hygromycin at a concentration of 200 µg/ml and individual resistant clones picked after two weeks of selection. ENV expression was characterized for each clone by Northern analysis and the highest-expressing ENV line subsequently cotransfected with a construct containing any of a number of linearized LTR vectors in combination with a linearized vector encoding blasticidin resistance in a 10:1 ratio (all linearized with ScaI). Cells were selected in blasticidin at a concentration of 40 µg/ml for two weeks and individual resistant clones picked. The clones were expanded and a representative sample of each was frozen back for future transfection of mutant integrase fusion constructs. Each clone was subsequently transfected with a construct linearized by digestion with ScaI encoding HXM resistance and the wild-type viral gag, polymerase and integrase genes under the regulation of a constitutive promoter and selected in 7.5 µg/mL hypoxanthine, 125 µg/mL xanthine and 12.5 µg/mL mycophenolic acid (0.5× HXM) for 2 weeks. HXM resistant colonies were pooled from individual electroporations and viral titers determined as described below. Viral producing lines exhibiting the highest titers were noted (suggesting efficient LTR transcription and packaging) and the corresponding line which lacked wild-type gag, polymerase and integrase sequences subsequently transfected with a ScaI linearized vector encoding HXM resistance and gag, polymerase and mutant integrase genes and selected as described above. Individual clonal viral packaging lines resulting from said selection were isolated, expanded and titered. Several lines for each mutant integrase and LTR construct exhibited observable titers demonstrating the construction of infection-competent mutant viral particles containing chimeric integrase and gene-trapping constructs. These packaging lines were expanded and large-scale infections subsequently performed as described below.

6.2 Demonstration of Partial Rescue of Truncated Integration Capabilities by the Addition of Transcription Factor (T.F.) Sequences.

In order to determine whether the addition of DNA binding protein sequences to truncated INT might rescue the integration capabilities of truncated integrase, viral packaging lines were constructed using a plasmid containing VICTR A as well as wild-type or mutant INT constructs to assess relative colony numbers resulting from infections with each of the individually pooled viral producers. As described above, a murine 3T3 fibroblast cell line previously characterized as expressing the retroviral envelope protein was electroporated with a plasmid encoding blasticidin resistance and VICTR A in a 1:10 ratio and blasticidin resistant clones isolated and expanded two weeks after transfection. Plasmids containing sequences encoding the integrase/p53 or glucocorticoid receptor (G.R.) fusion proteins mentioned above, wild-type integrase or integrase containing a stop codon at the NdeI fusion site (see FIG. 1) were subsequently linearized with ScaI and electroporated into the above lines and selected in 0.5× HXM as described above. HXM resistant colonies were pooled from individual electroporations and viral titers as well as integration specificity determined as described below.

Packaging cells generated from the above transfections were plated at an equal density of $3.0 \times 10^6$ cells/150 mm plate 24 hours prior to the addition of ES cell media. 18 ml media was added to the viral producers 24 hours prior to infection. At the time of infection media was removed from each packaging line and filtered through a 0.2 $\mu$m filter. Polybrene was added at a concentration of 8 $\mu$g/ml and the virus-containing media overlaid, in duplicate, onto AB2.2 embryonic stem cells at a cellular density of $2.0 \times 10^6$ cells/100 mm dish. Infections were allowed to occur overnight and 24 hours post-infection cells were rinsed in PBS and media containing neomycin was added at a concentration of 180 $\mu$g/ml. Positive clones were allowed to grow for approximately 10 days before being stained and counted.

The graph in FIG. 7 depicts the average number of colonies present from each infection. A strong bias in cell survival and resulting colony formation of approximately 12–15 fold is observed for the cells infected with fusions of either full length p53 or the glucocorticoid receptor DNA binding domain to the Nde1 site of INT as compared to the INT construct containing the stop codon at this site. These data suggest that by providing additional transcription factor coding sequences at the Nde1 junction of INT successful retroviral integration has been enhanced, theoretically through interaction, either direct or indirect, with target regulatory elements.

6.3 Repeat Rate Observed for Wild-type and p53 or Glucocorticoid Receptor Modified Retroviruses.

To assess the potential for possible "hot spot" target loci susceptible to repeated integration and subsequent trapping, the repeat rates of loci trapped by VICTR3 were analyzed resulting for both INT/p53 and INT/glucocorticoid receptor fusion containing viral particles and compared to wild-type control rates statistically. Viral packaging lines containing either wild-type, p53-modified or G.R.-modified integrase and the gene trapping construct VICTR3 (see FIG. 2) were used to infect AB2.2 embryonic stem cells as described above. Resulting puromycin-resistant clones were assayed for trapped target genes by the following procedure: Total RNA was isolated from an aliquot of cells from each of 10 gene trap clones chosen for study. 5 $\mu$g of this RNA was used in a first strand cDNA synthesis reaction using the "RS" primer. This primer has unique sequences (for subsequent PCR) on its 5' end and nine random nucleotides or nine T (thymidine) residues on it's 3' end. Reaction products from the first strand synthesis were added directly to a PCR reaction with outer primers specific for the engineered sequences of puromycin and the "RS" primer. After amplification, an aliquot of reaction products was subjected to a second round of amplification using primers internal, or nested, relative to the first set of PCR primers. This second amplification provided more reaction product for sequencing and also provided increased specificity for the specifically gene trapped DNA.

The products of the nested PCR were visualized by agarose gel electrophoresis. Those resulting in PCR products were sequenced directly after excess PCR primers and nucleotides were removed by filtration in a spin column (Centricon-100, Amicon). DNA was added directly to dye-terminator sequencing reactions (purchased from ABI) using the standard M13 forward primer, a region for which was built into the end of the puro exon in all of the PCR fragments.

For analysis of repeat rate, nucleotide sequences obtained from the above reactions were imported into Sequencer™ 3.0 and searched against one another for significant homologous regions, suggesting that LTR constructs had integrated into the same genomic location. To prevent a bias in the analysis, all repetitive elements were removed from mutant sample populations. Given the small sample sets accumulated for three different INT/p53 fusion constructs, all samples were combined and the resulting repeat rate compared to that for wild-type integrase utilizing a Fisher statistical analysis. The observed repeat rate for all p53 targets combined was 51.9% compared to 7.4% for wild-type integrase (FIG. 8). Fisher analysis gave a p value of 0.005 suggesting a significant difference in the rates between the two populations. Repeat rates for two fusions between integrase and the glucocorticoid receptor were characterized and compared to that for wild-type integrase using a $\chi 2$ analysis (FIG. 9). The rate observed for the G.R. DNA binding domain fused to the NdeI truncated site of integrase of 14% was significantly higher than that observed for wild-type integrase, which for a similar sample population was 5%. A comparison of the two sample sets gave a p value of <0.02. A statistical comparison of the G.R. DNA binding domain fusion to the terminal end of INT with that of wild-type integrase did not reveal a significant difference in repeat rates suggesting that not all INT/T.F. fusions function optimally to direct integration (FIG. 9). These data suggest that LTR integration is targeted to potential "hot spots", i.e. putative target genes within the genome by specific INT/p53 or INT/G.R. fusions as compared to controls.

6.4 Nucleotide Sequence of Target Genes Trapped by T.F.-Modified Retroviruses.

Viral packaging lines containing the integrase/p53 or integrase/G.R. fusion constructs and VICTR 3 were used to infect AB 2.2 embryonic stem cells and the resulting trapped genes analyzed as described above. FIG. 10A depicts the BLAST (basic local alignment search tool) output for the query sequence and reveals that the trapped gene is highly homologous to rat ICE. The protein encoded by this gene has previously been shown to be involved in and required for p53 dependent apoptosis (Rao et al., 1996, *J Cell Biol*, 135:1441–55; Sabbatini et al., 1997, *Cell Growth and Differentiation*, 8:643–653). FIG. 10B reveals the sequence of the intronic location where the LTR trapping construct integrated. The sequence displays an as yet unpublished p53 binding site (highlighted) which fits the half-site consensus and is 2 nucleotides from the full length p53 consensus binding site, suggesting targeted retroviral integration mediated through interaction of the INT/p53 fusion protein with this regulatory element. As further validation of the presently described method of targeted gene discovery, several known genes were also identified as associated with p53 target sequences. These genes include the p22 subunit of TFIID, BMKI, ubiquitin conjugating enzyme, myosin light chain 2A, integral membrane protein CII-3, and the activin receptor type IIB.

Additionally, several known targets for modulation of expression of glucocorticoids have been trapped by the INT/G.R. fusions. These include superoxide dismutase (Valentine et al., 1994, *Gastroenterology* 107: 1662–70), beta dehydrogenase (Low et al., 1994, *J. Neuroendocrinol.* 6:285–90) and what appears to be a novel cyclooxygenase (O'Banion et al., 1991, *J. Biol. Chem.* 266: 23261–7) (homologies not shown). Other known genes identified as targets for the glucocorticoid receptor include flt3 ligand, cytosolic acyl coenzyme A thioester hydrolase, suppressor of MIF2, renin binding protein, parathymosin alpha, TATA binding protein DR1, eyes absent, rard 3, taxi binding protein, cytoplasmic phosphotyrosine phosphatase, galectin-7, GDP dissociation inhibitor, bactenecin, the glucagon receptor, Btk, beta dehydrogenase, aspartate amidohydrolase, MSI, ATP synthase, ATPase inhibitor, translational initiation factor, FK506 immunophilin, gap modifying protein, pituitary glycoprotein hormone, trefoil factor, preproneurterin and capping protein beta subunit isoform 2.

While the above data reveal potential target genes for regulation by p53 or the glucocorticoid receptor, the present invention is in no way limited to these particular targets or particular transcription factors. In fact, the present methods are particularly useful for the identification of novel genes that encode previously undiscovered polypeptides.

Taken together, the above data demonstrate: 1) the production of a chimeric integrase that incorporates a DNA binding domain from a biologically relevant protein with known function in the target cell; 2) that chimeric integrase may be incorporated into an infectious viral particle; 3) that the presence of the chimeric integrase does not interfere with reverse transcription; 4) that the chimeric integrase retains the ability to process the inverted repeats at both ends of the retroviral DNA product of reverse transcription; and 5) that the chimeric integrase can direct the nonrandom, or biased, integration of the retroviral genome to targeted regions of the cellular genome.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above described modes for carrying out the invention which are obvious to those skilled in the field of molecular biology or related fields are intended to be within the scope of the following claims.

What is claimed is:

1. An infectious virus comprising:
   a) a chimeric integrase;
   b) a 3' gene trap cassette comprising in operable combination:
      1) a promoter;
      2) an exon sequence located 3' from and expressed by said promoter; and
      3) a splice donor sequence defining the 3' region of the exon; and
   wherein said cassette does not encode a sequence that mediates the polyadenylation of an mRNA transcript encoded by said exon sequence and expressed by said promoter.

2. The infectious virus of claim 1, further comprising a selectable marker.

3. A collection of cultured embryonic stem cells wherein
   a) each cell has a polynucleotide of the infections virus according to claim 1 integrated into its genome;
   b) the cells of said collection are physically separated so that clonally derived colonies of cells are created;
   c) at least about 200 base pairs of a trapped cellular sequence from at least about 96 of said colonies have been determined; and
   d) said collection of embryonic stem cells comprises at least about 96 colonies; and
   wherein the cultured embryonic stem cells are derived from mouse.

4. A method of generating a collection of cultured embryonic stem cells comprising
   a) integrating into the genome of cultured embryonic stem cells a polynucleotide of the infections virus according to claim 1;

b) physically separating said cells, following the integration of said gene trapping vector, so that at least about 96 clonally derived colonies of cells are created; and c) sequencing at least about 200 base pairs of a trapped cellular sequence from at least about 96 of said colonies; and wherein the cultured embryonic stem cells are derived from mouse.

5. A collection of cultured embryonic stem cells wherein a) each cell has a gene trapping vector integrated into its genome, wherein said gene trapping vector comprises a chimeric integrase;

b) the cells of said collection are physically separated so that clonally derived colonies of cells are created;

c) at least about 200 base pairs of a trapped cellular sequence from at least about 96 of said colonies have been determined;

d) said collection of embryonic stem cells comprises at least about 96 colonies; and wherein the cultured embryonic stem cells are derived from mouse.

6. A method of generating a collection of cultured embryonic stem cells comprising a) integrating into the genome of cultured embryonic stem cells a gene trapping vector comprising a chimeric integrase;

b) physically separating said cells, following the integration of said gene trapping vector, so that at least about 96 clonally derived colonies of cells are created;

c) sequencing at least about 200 base pairs of a trapped cellular sequence from at least about 96 of said colonies; and wherein the cultured embryonic stem cells are derived from mouse.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 39 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:1:

GGGGAAGAAA GGGTTAATTC GACTTACCCT TCCACATTG    39

(2) INFORMATION FOR SEQ ID NO:2:

(i) SEQUENCE CHARACTERISTICS:
        (A) LENGTH: 39 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:2:

GGGGAAGAAA GGGTTTATTT GGCTTACACT TCCACATTG    39

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:3:

TTGTTCATCA CCAAGGAATT CAGGACTGGA ACTCAATCA                39

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:4:

CTGTTCATCA CCAAATGAGT CAGAACAGGA ACTCACACA                39

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:5:

GGTCTGGAAG CATGAGCTGA T                              21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:6:

GGGCAGGAAG CAGGAGCTGA T                              21

(2) INFORMATION FOR SEQ ID NO:7:

(i) SEQUENCE CHARACTERISTICS:
        (A) LENGTH: 47 base pairs
        (B) TYPE: nucleic acid
        (C) STRANDEDNESS: unknown
        (D) TOPOLOGY: linear (ii) MOLECULE TYPE: DNA (genomic)

-continued

```
    (iv) ANTI-SENSE: NO (xi) SEQUENCE DESCRIPTION: SEQ ID NO:7:

AAATTATAGA ACTACACTGT ACATTATTCT GATTGGTTTT TTTGTTT                    47

(2) INFORMATION FOR SEQ ID NO:8:

(i) SEQUENCE CHARACTERISTICS:
        (A) LENGTH: 47 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:8:

GTTTTTTGTT TTGCTTTGAT TTTAAGATAC AGTCTCACTA TTTAGAC                    47

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:9:

AGGCTAGCCT CCAGCTTACA AAGATCTGCC TGCCTCTGCT CCCTG                      45

(2) INFORMATION FOR SEQ ID NO:10:

(i) SEQUENCE CHARACTERISTICS:
        (A) LENGTH: 44 base pairs
        (B) TYPE: nucleic acid
        (C) STRANDEDNESS: unknown
        (D) TOPOLOGY: linear (ii) MOLECULE TYPE: DNA (genomic)

(iv) ANTI-SENSE: NO (xi) SEQUENCE DESCRIPTION: SEQ ID NO:10:

TGTGGTGGGA CTAAAGGCAT GCGCTACCCA CCCCCAGCTG CTTA                       44
```